US012673076B2

(12) United States Patent
O'Hara

(10) Patent No.: US 12,673,076 B2
(45) Date of Patent: *Jul. 7, 2026

(54) LACTOBACTILUS PLANTARUM 2830 (ECGC 13110402) FOR USE IN TREATMENTS

(71) Applicant: PROBIOTIX HEALTH LIMITED, Pontefract (GB)

(72) Inventor: Stephen Patrick O'Hara, Heslington (GB)

(73) Assignee: PROBIOTIX LIMITED, Wakefield (GB)

( * ) Notice: Subject to any disclaimer, the term of this patent is extended or adjusted under 35 U.S.C. 154(b) by 186 days.

This patent is subject to a terminal disclaimer.

(21) Appl. No.: 15/034,500

(22) PCT Filed: Nov. 5, 2014

(86) PCT No.: PCT/GB2014/053302

§ 371 (c)(1),
(2) Date: May 4, 2016

(87) PCT Pub. No.: WO2015/067948

PCT Pub. Date: May 14, 2015

(65) Prior Publication Data

US 2016/0271191 A1     Sep. 22, 2016

(30) Foreign Application Priority Data

Nov. 5, 2013     (GB) ...................................... 1319538

(51) Int. Cl.
*A61K 35/747*     (2015.01)
*A23L 33/10*     (2016.01)
(Continued)

(52) U.S. Cl.
CPC ............ *A61K 35/747* (2013.01); *A23L 33/10* (2016.08); *A23L 33/135* (2016.08); *A23L 33/21* (2016.08); *A61K 38/43* (2013.01); *A23V 2002/00* (2013.01)

(58) Field of Classification Search
CPC ....... A61K 35/747; A61K 38/43; A23L 33/10; A23L 33/135; A23L 33/21;
(Continued)

(56) References Cited

U.S. PATENT DOCUMENTS 6,214,336 B1 *  4/2001  Bukowska ................ A61P 7/02
                                                           424/93.45
8,486,668 B2 *  7/2013  Ritter ...................... A61P 19/10
                                                           435/101
(Continued)

FOREIGN PATENT DOCUMENTS

EP     0 856 259 A1     8/1998
EP     2 216 036 A1     8/2010
(Continued)

OTHER PUBLICATIONS

Park et al., J. Microbiol. Biotechnol.2007 ; 17(4), pp. 655-662.*
(Continued)

*Primary Examiner* — Tracy Vivlemore
*Assistant Examiner* — Lauren K Van Buren
(74) *Attorney, Agent, or Firm* — Nicholas P. Stadnyk; Maynard Nexsen PC

(57) ABSTRACT

The present invention relates to one or more strains of *Lactobacilli* and a cholesterol modifying agent (such as an oligosaccharide) for use in modifying the absorption of cholesterol in an individual or the treatment of heart disease, diabetes or obesity.

8 Claims, 15 Drawing Sheets

(51) Int. Cl.
| | |
|---|---|
| *A23L 33/135* | (2016.01) |
| *A23L 33/21* | (2016.01) |
| *A61K 38/43* | (2006.01) |

(58) Field of Classification Search
CPC .......... A23V 2002/00; A61P 3/04; A61P 3/06; A61P 3/10; A61P 9/00; A61P 43/00
See application file for complete search history.

(56) References Cited

U.S. PATENT DOCUMENTS

| | | | | |
|---|---|---|---|---|
| 8,668,906 | B2 * | 3/2014 | Cune ...................... | A61K 35/74 |
| | | | | 424/93.45 |
| 10,463,704 | B2 * | 11/2019 | O'Hara ................... | A61P 43/00 |
| 10,898,528 | B2 * | 1/2021 | O'Hara ..................... | A61P 9/00 |
| 2004/0115179 | A1 | 6/2004 | Liu et al. | |
| 2008/0254011 | A1 | 10/2008 | Rothschild et al. | |
| 2009/0214594 | A1 | 8/2009 | Fichot et al. | |
| 2011/0117629 | A1 | 5/2011 | Lin et al. | |
| 2011/0177044 | A1 | 7/2011 | Thomas et al. | |
| 2011/0206649 | A1 | 8/2011 | Deonda et al. | |
| 2012/0213753 | A1 | 8/2012 | Castellana | |
| 2012/0263696 | A1 | 10/2012 | Roos | |
| 2013/0089633 | A1 | 4/2013 | Nakamura et al. | |

FOREIGN PATENT DOCUMENTS

| | | | |
|---|---|---|---|
| EP | 2729152 | B1 | 12/2015 |
| JP | 2012-100655 | A | 5/2012 |
| WO | 99007827 | A1 | 2/1999 |
| WO | 2004/074496 | A1 | 9/2004 |
| WO | 2010098822 | A1 | 9/2010 |
| WO | 2010/124387 | A1 | 11/2010 |
| WO | 201042333 | A1 | 4/2011 |

OTHER PUBLICATIONS

Gobinath et al. "Permeabilized probiotic Lactobacillus plantarum as a source of beta-glucosidase for the synthesis of prebiotic galactooligosaccharides" Biotechnol Lett (2014) 36: 153-157. (Year: 2014).*

International Search Report and Written Opinion issued in corresponding International Application No. PCT/GB2014/053303 mailed Feb. 4, 2015.

International Search Report and Written Opinion issued in corresponding International Application No. PCT/GB2014/053290 mailed Feb. 4, 2015.

International Search Report and Written Opinion issued in corresponding International Application No. PCT/GB2014/053301 mailed Feb. 4, 2015.

International Search Report and Written Opinion issued in corresponding International Application No. PCT/GB2014/053302 mailed Feb. 4, 2015.

Al-Fataftah, A. et al., "Enrichment of vitamin B12 and B6 and lowering cholesterol levels of eggs by lactic acid bacteria", International Journal of Food, Agriculture & Environment, vol. 11, No. 2, Jan. 1, 2013, pp. 674-678, XP55158928, Helsinki, ISSN: 1459-0255.

Al-Fataftah, A. et al., "Administration of lactic acid bacteria to enhance synthesis of vitamin B12 and B6 and lower cholesterol levels in poultry meat", International Journal of Food, Agriculture & Environment, vol. 11, No. 2, Jan. 1, 2013, pp. 604-609, XP55158929, Helsinki, ISSN: 1459-0255.

Kumar R., et al., "Bile Salt Hydrolase (Bsh) Activity Screening of Lactobacilli: In Vitro Selection of Indigenous Lactobacillus Strains with Potential Bile Salt Hydrolysing and Cholesterol-Lowering Ability", Probiotics and Antimicrobial Proteins, vol. 4, No. 3, Sep. 1, 2012, pp. 162-172, XP002734609.

Liong, M.T. et al., "Bile salt deconjugation ability, bile salt hydrolase activity and cholesterol co-precipitation ability of lactobacilli strains", International Dairy Journal, Elsevier Applied Science, Barking, GB, vol. 15, No. 4, Apr. 1, 2005, pp. 391-398, XP004715114, ISSN: 0958-6946.

Pereira, D.I.A., et al., "An In Vitro Study of the Probiotic Potential of a Bile-Salt-Hydrolyzing Lactobacillus fermentum Strain, and Determination of Its Cholesterol-Lowering Properties", Applied and Environmental Microbiology, vol. 69, No. 8, Aug. 1, 2003, pp. 4743-4752, XP055163574, ISSN: 0099-2240.

Rabiu, B.A., et al., "Synthesis and fermentation properties of novel galacto-oligosaccharides by beta-galactosidases from *Bifidobacterium* species", Applied and Environmental Microbiology, American Society for Microbiology, US, vol. 67, No. 6, Jun. 1, 2001, pp. 2526-2530, XP002613005, ISSN: 0099-2240.

Splechtna, B., et al., "Production of Prebiotic Galacto-Oligosaccharides from Lactose Using [beta]-Galactosidases from Lactobacillus reuteri", Journal of Agricultural and Food Chemistry, vol. 54, No. 14, Jul. 1, 2006, pp. 4999-5006, XP055161581, ISSN: 0021-8561.

Tzortzis, G. et al. "In vitro evaluation of the fermentation properties of galactooligosaccharides synthesized by [alpha]-galactosidase from Lactobacillus Reuteri", Applied Microbiology and Biotechnology, Springer, DE, vol. 64, No. 1, Jan. 1, 2004 (Jan. 1, 2004), pp. 106-111, XP002285616, ISSN: 0175-7598, DOI: 10.1007/S00253-003-1427-Z.

Park, Yoo Heon et al. "Effect of Dietary Inclusion of Lactobacillus acidophilus ATCC 43121 on Cholesterol Metabolism in Rats", Journal of Microbiology and Biotechnology, vol. 17, No. 4, Apr. 1, 2007 (Apr. 1, 2007), pp. 655-662, XP002734586, Seoul , Korea ISSN: 1017-7825.

Noh, D. O. et al. "Incorporation of Cholesterol into the Cellular Membrane of Lactobacillus acidophilus ATCC 43121", Journal of Dairy Science, American Dairy Science Association, US, vol. 80, No. 12, Dec. 1, 1997 (Dec. 1, 1997), pp. 3107-3113, XP027048111, ISSN: 0022-0302.

Kondo Shizuki et al. "Approaches in the Development of Probiotics for Improving Metabolic Disorders", Food Science and Technology Institute, 2010, vol. 24, pp. 281-286, 6 pages.

Notice of Opposition corresponding to European Patent Application. 14806046.0, mailed Jun. 18, 2020, 152 pages.

Extract from ARCC catalogue of "Lactobacillus Acidophilus (Moro) Hansen and Mocquot (ATCC 43121)", 1 page.

Gilliland S.E. et al. "Assimilation of Cholesterol by Lactobacillus acidophilus", Applied and Environmental Microbiology, Feb. 1985, vol. 49, No. 2, p. 377-381, 5 pages.

Jones Mitchell L et al. Cholesterol lowering with bile salt hydrolase-active probiotic bacteria, mechanism of action, clinical evidence, and future direction for heart health applications, Expert Opinion on Biological Therapy, Jan. 28, 2013, vol. 13 No. 5, pp. 631-642, 13 pages.

Ducrotte Philippe et al. "Clinical trial: Lactobacillus Plantarum 299v (DSM 9843) improves symptoms of irritable bowel syndrome", World Journal Gastroenterology, Aug. 14, 2012, vol. 18 No. 30, pp. 4012-4018, 7 pages.

Ogue-Bon Eva et al. "In vitro effects of synbiotic fermentation on the canine faecal microbiota", Federation of European Microbiological Societies (FEMS) Microbiology Ecology, Jun. 23, 2010, vol. 73, pp. 587-600, 14 pages.

Okubo Takuma et al. "KK/Ta Mice Administered Lactobacillus plantarum Strain No. 14 Have Lower Adiposity and Higher Insulin Sensitivity", Bioscience of Microbiota, Food and Health, 2013, vol. 32 No. 3, pp. 93-100, 8 pages.

Buck Lys M. et al. "Comparisons of Freshly Isolated Strains of Lactobacillus acidophilus of Human Intestinal Origin for Ability to Assimilate", Journal of Dairy Science, 1994, vol. 77 No. 10, pp. 2925-2933, 9 pages.

Ha Chul-Gyu et al. "Cholesterol Lowering Effect of Lactobacillus plantarum Isolated from Human Feces", Journal of Microbiology and Biotechnology, 2006, vol. 16 No. 8, pp. 1201-1209, 9 pages.

Vulevic Jelena et al. "A Mixture of trans-Galactooligosaccharides Reduces Markers of Metabolic Syndrome and Modulates the Fecal Microbiota and Immune Function of Overweight Adults", Jan. 9, 2013, pp. 324-331, 8 pages.

(56)                 References Cited

OTHER PUBLICATIONS

Stephens K et al. "Development of a synergistic synbiotic for Lactobacillus plantarum LP-LDL targeting cholesterol reduction", Department of Food and Nutritional Sciences, 2017, 1 page.

DiRienzo Douglas B et al. "Effect of probiotics on biomarkers of cardiovascular disease: implications for heart-healthy diets", Nutrition Reviews, 2014, vol. 72 No. 1, pp. 18-29, 12 pages.

Xie Ning et al. "Effects of two Lactobacillus strains on lipid metabolism and intestinal microflora in rats fed a high-cholesterol diet", BMC Complementary and Alternative Medicine, 2011, vol. 11 No. 53, 11 pages.

Fuentes Mari C. et al. "Cholesterol-lowering efficacy of Lactobacillus plantarum CECT 7527, 7528 and 7529 in hypercholesterolaemic adults", 2013, vol. 109, pp. 1866-1872, 7 pages.

LPLDL Brochure, OptiBiotix Health Plc, 2018, 2 pages.

Molenaar Douwe et al. "Exploring Lactobacillus plantarum Genome Diversity by Using Microarrays", Journal of Bacteriology, Sep. 2005, vol. 187 No. 17, pp. 6119-6127, 9 pages.

Siezen Roland J et al. "Genomic diversity and versatility of Lactobacillus plantarum, a natural metabolic engineer", Microbial Cell Factories, vol. 10 Supp 1:S3, 13 pages, 2011.

Costabile Adele et al. "An in vivo assessment of the cholesterol lowering efficacy of Lactobacillus plantarum ECGC 13110402 in normal to mildly hypercholesterolaemic adults", PLOS One, vol. 12 No. 12, Dec. 11, 2017, 21 pages.

Proprietor's Submission in Response to the Opposition Division's Preliminary Opinion in Advance of Oral Proceedings corresponding to European Patent No. 3065571, dated Jul. 5, 2023, 3 pages.

Begley et al "Bile Salt Hydrolase Activity in Probiotics", Applied and Environmental Microbiology, Mar. 2006, 1729-1738.

Dong, Z et al.,"A bile salt hydrolase gene of lactobacillus plantarum BBE7 with high cholesterol-removing activity", Eur Food Res Technol. 2012, vol. 235 pp. 419-427.

De Smet, et al.. "In vitro study of bile salt hydrolase (BSH) activity of BSH isogenic lactobacillus plantarum 80 strains and estimation of cholesterol lowering through enhanced BSH activity", Microbial Ecology in Health and Disease, 1994, vol. 7-6 pp. 315-329.

Sanaullah,I.et al., Carbohydrate Research, (2010) vol. 345 pp. 1408-1416.

J. Dairy Sci., 1996, vol. 79, pp. 2121-2128.

* cited by examiner

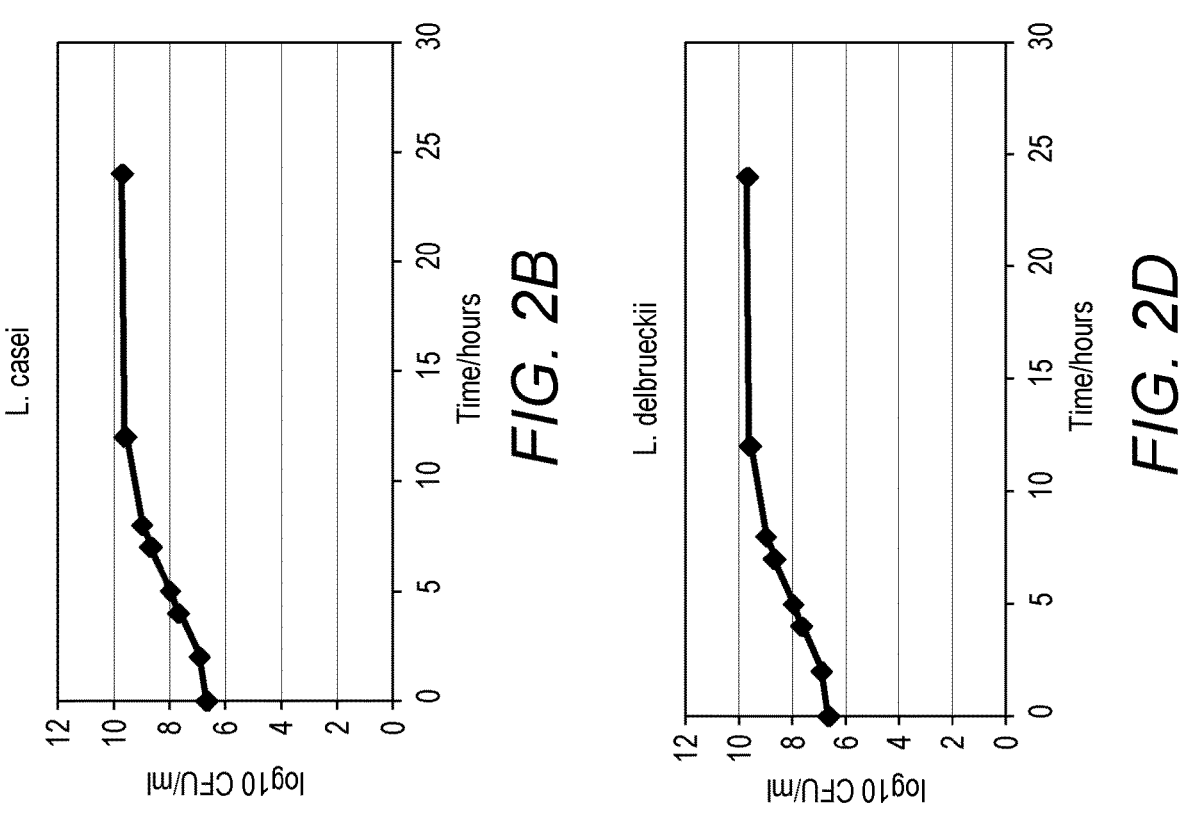
*FIG. 2B*
*FIG. 2D*
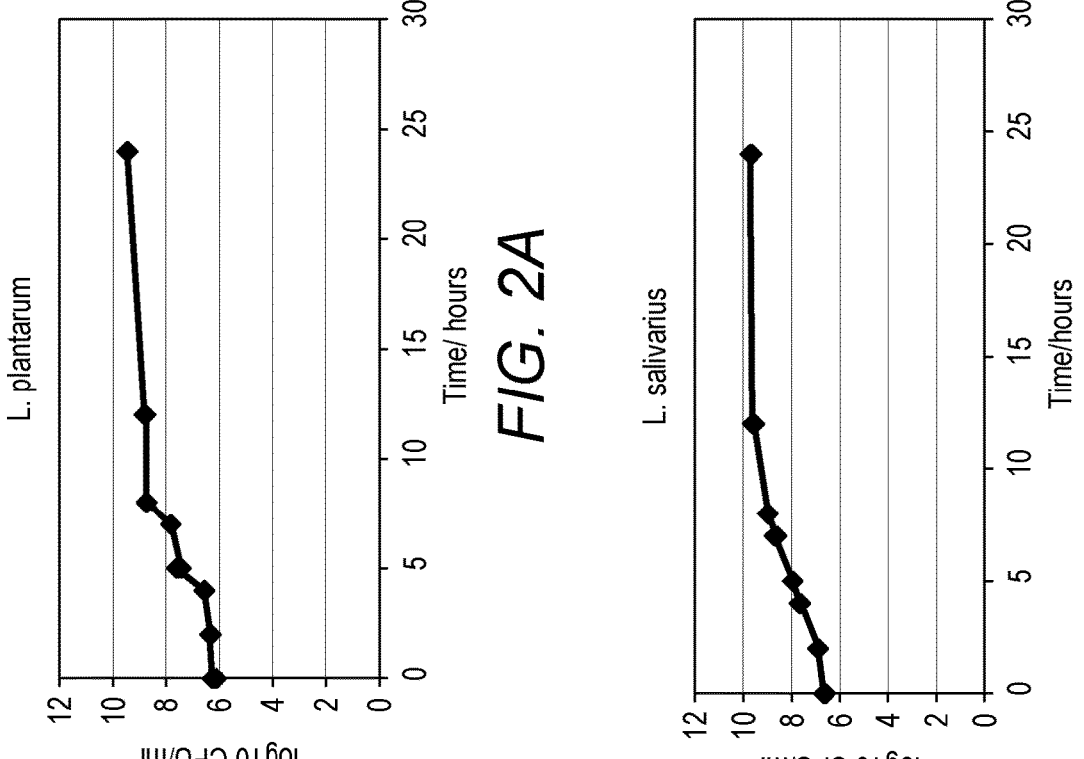
*FIG. 2A*
*FIG. 2C*

Average OD$_{600}$ of the lactobacilli strains in 0.4% oxgall and 100mg/L cholesterol concentration in MRS media

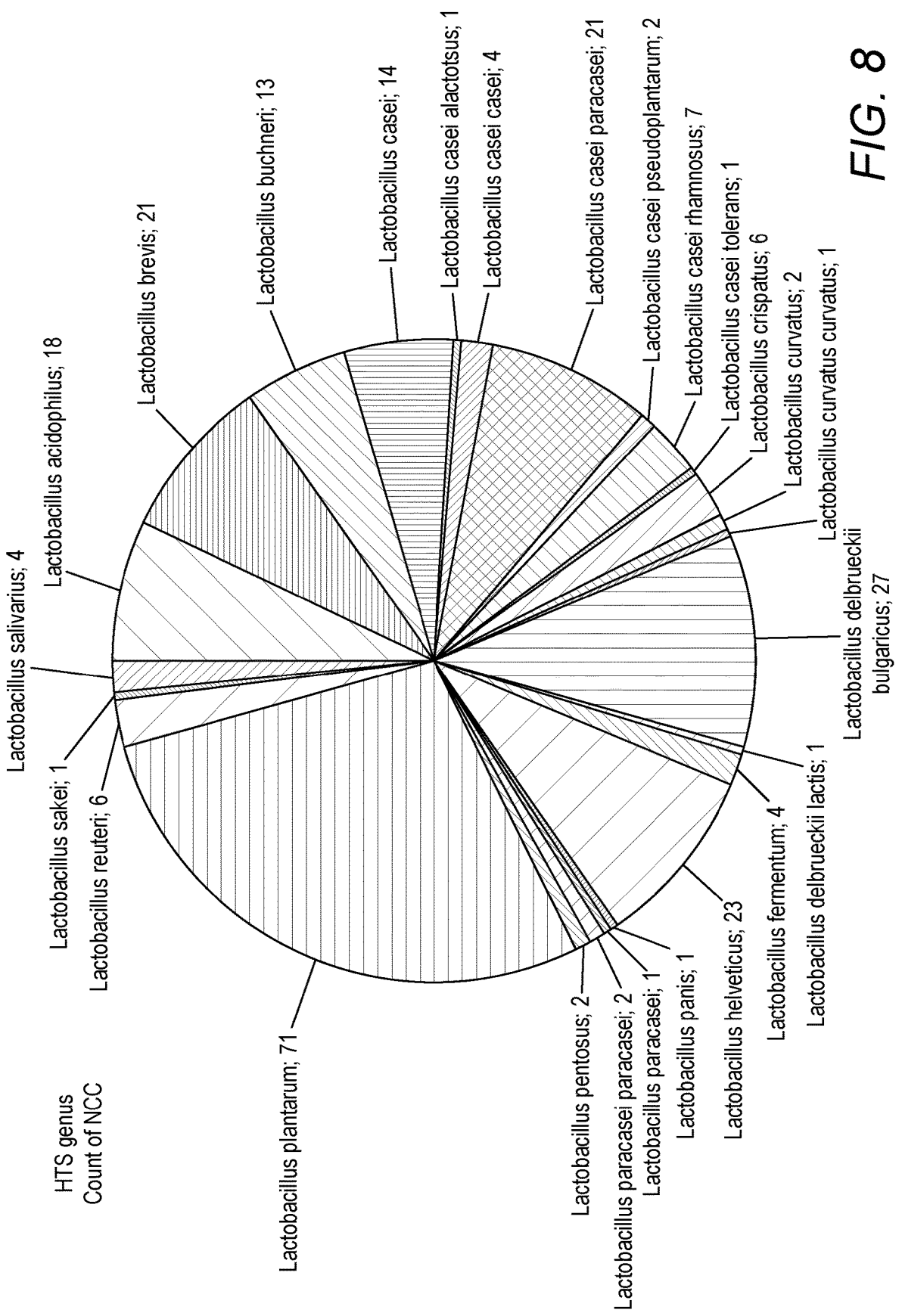

HTS genus
Count of NCC

Lactobacillus acidophilus; 18
Lactobacillus brevis; 21
Lactobacillus buchneri; 13
Lactobacillus casei; 14
Lactobacillus casei alactotsus; 1
Lactobacillus casei casei; 4
Lactobacillus casei paracasei; 21
Lactobacillus casei pseudoplantarum; 2
Lactobacillus casei rhamnosus; 7
Lactobacillus casei tolerans; 1
Lactobacillus crispatus; 6
Lactobacillus curvatus; 2
Lactobacillus curvatus curvatus; 1
Lactobacillus delbrueckii bulgaricus; 27
Lactobacillus delbrueckii lactis; 1
Lactobacillus fermentum; 4
Lactobacillus helveticus; 23
Lactobacillus panis; 1
Lactobacillus paracasei; 1
Lactobacillus paracasei paracasei; 2
Lactobacillus pentosus; 2
Lactobacillus plantarum; 71
Lactobacillus reuteri; 6
Lactobacillus sakei; 1
Lactobacillus salivarius; 4

FIG. 8

LACTOBACTILUS PLANTARUM 2830 (ECGC 13110402) FOR USE IN TREATMENTS

CROSS REFERENCE TO RELATED APPLICATIONS

This application is a U.S. National Phase of PCT/GB2014/053302, filed Nov. 5, 2014, which claims priority to Great Britain Application No. 1319538.3, filed Nov. 5, 2013, each of which is incorporated herein by reference in its entirety.

TECHNICAL FIELD OF THE INVENTION

The invention relates to a probiotic and prebiotic composition which is useful in the management of cholesterol levels.

BACKGROUND TO THE INVENTION

Probiotics are bacteria which confer health benefits to a host. Typically, cultures of probiotic bacterial strains are consumed or administered to individuals in order to supplement the naturally occurring bacteria population of the gut. A number of health benefits have been associated with probiotics, including reducing the incidence of cancer, diarrhoea and irritable bowel syndrome to name a few. Probiotics have the potential to help in the management in a number of physiological conditions and act to reduce the absorption of certain ingested substances, such as lipids. Preliminary studies also indicate that probiotics can be useful in reducing serum levels of cholesterol and blood pressure and help modulate diabetes and reduce weight.

*Lactobacilli* are common probiotics in diary products and make up approximately 75% of probiotics currently sold. However, it has been estimated that only 2% of *Lactobacilli* dose survives be effective in the gut.

Prebiotics are dietary ingredients which can selectively enhance beneficial indigenous gut microbiota, such as lactobacilli or bifidobacteria, and are finding much increased application into the food sector. Prebiotics are non digestible food ingredients that are selectively metabolised by colonic bacteria which contribute to improved health. As such, their use can promote beneficial changes within the indigenous gut microbial milieu and they can therefore help survivability of probiotics. They are distinct from most dietary fibres like pectin, celluloses, xylan, which are not selectively metabolised in the gut. Criteria for classification as a prebiotic is that it must resist gastric acidity, hydrolysis by mammalian enzymes and gastrointestinal absorption, it is fermented by intestinal microflora and selectively stimulates the growth and/or activity of intestinal bacteria associated with health and well-being.

Fructo-oligosaccharides (FOS, inulin and oligofructose) and galactooligosaccharides (GOS) have been demonstrated to fulfil the criteria for prebiotic classification repeatedly in human intervention studies. Currently, no prebiotic for *Lactobacilli* exists.

It is an object of the present invention to provide a combination of a *Lactobacilli* probiotic and specific prebiotic for the *Lactobacilli* which would be suitable for use in modifying the absorption of cholesterol in an individual. It would also be beneficial if the probiotic composition could also be used to treat other physiological conditions, such as heart disease, diabetes or obesity.

SUMMARY OF THE INVENTION

In accordance with a first aspect of the present invention, there is provided a composition comprising a strain or strains of *Lactobacilli* having an elevated bile salt hydrolase activity and a cholesterol modifying agent.

In accordance with a further aspect of the present invention, there is provided a composition for use in modifying the absorption of cholesterol in an individual comprising a strain or strains of *Lactobacilli* having an elevated bile salt hydrolase activity and a cholesterol modifying agent.

In accordance with yet another aspect of the present invention, there is provided a composition for use in the treatment of high cholesterol, heart disease, diabetes or obesity comprising a strain or strains of *Lactobacilli* having an elevated bile salt hydrolase activity and a cholesterol modifying agent.

In accordance with yet a further aspect of the present invention, there is provided the use of a composition in the manufacture of a medicament for the treatment of high cholesterol, heart disease, diabetes or obesity, wherein the composition comprises a strain or strains of *Lactobacilli* having an elevated bile salt hydrolase activity and a cholesterol modifying agent For any aspect, the strain or strains of the composition may comprise at least one strain selected from *Lactobacillus plantarum* 2828 (ECGC 13110403); *Lactobacillus plantarum* 2830 (ECGC 13110402); and *Lactobacillus plantarum* 2691 (ECGC 13110401); and *Lactobacillus acidophilus* ATCC 43121 or mutant strains thereof.

The term "mutant strain" in the context of this patent application is intended to mean any strains which are directly derived from those strains disclosed, but which are phenotypically different due to the introduction of one or more genetic mutations (whether by genetic engineering or selection).

The cholesterol modifying agent comprises oligosaccharides. Preferably, the oligosaccharide is selected from one or more of the following: β-galactosidases, α-galactosidases, α- and β-glucosidases, α-mannosidases, or β-xylosidases. More preferably, the bacterial strain is capable of producing the oligosaccharides by reverse enzyme reaction.

The cholesterol modifying agent may comprise a selective growth medium for the strain or strains of *Lactobacilli*.

The composition may further comprise a prebiotic or a secondary prebiotic if the cholesterol modifying agent comprises a prebiotic.

The probiotic composition will preferably be present in the composition in an effective amount so as to elicit a change in the absorption profile of cholesterol in the small intestine. Preferably, the cultures will be administered to an individual in an amount in the range of $10^5$ cfu/g to $10^{12}$ cfu/g. More preferably, the probiotic bacterial strain is in an amount in the range of $10^8$ cfu/g to $10^9$ cfu/g. Although it will be appreciated that different dosages may be administered depending upon the individuals' condition.

The strain may be encapsulated. Many encapsulation techniques will be apparent to the skilled addressee and the one employed will be tailored to the required stability of the probiotic culture during digestive transit. The encapsulate may comprise a prebiotic specifically tailored to the probiotic.

The probiotic composition may further comprise an excipient or carrier compound to enable it to be released at the most appropriate time for reducing cholesterol absorption. Typically, the culture must survive relatively intact until it reaches the intestinal enterocytes of the small intestine.

The composition may be in a number of food stuff formats, such as a drinkable liquid, a spread and/or powder which can be mixed with a solid or liquid food stuff.

The composition may be combined with one or more active ingredients, such as vitamins, minerals, phytochemicals, antioxidants, and combinations thereof.

Vitamins may include fat soluble vitamins such as vitamin A, vitamin D, vitamin E, and vitamin and combinations thereof. In some embodiments, vitamins can include water soluble vitamins such as vitamin C (ascorbic acid), the B vitamins (thiamine or B 1, riboflavoin or B25 niacin or B3, pyridoxine or B6, folic acid or B9, cyanocobalimin or B12, pantothenic acid, biotin), and combinations thereof.

Minerals may include but are not limited to sodium, magnesium, chromium, iodine, iron, manganese, calcium, copper, fluoride, potassium, phosphorous, molybdenum, selenium, zinc, and combinations thereof.

Antioxidants may include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

Phytochemicals may include but are not limited to cartotenoids, chlorophyll, chlorophyllin, fiber, flavanoids, anthocyamns, cyaniding, delphinidin, malvidin, pelargonidin, peonidin, petunidin, flavanols, catechin, epicatechin, epigallocatechin, epigailocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

Alternative (or additionally) to a pharmaceutical or medicament, the composition may be used as a dietary supplement, a nutraceutical or a functional food. Furthermore, the composition could be incorporated into an existing food stuffs, such as yoghurt, food spread or as a powder which can be easily blended with foodstuffs or made into a liquid drink. The composition may also be formulated into to dietary supplement.

In accordance with a further aspect of the present invention, there is provided a method of producing the composition as herein above described, comprising mixing a strain or strains of *Lactobacilli* having an elevated bile salt hydrolase activity with a cholesterol modifying agent in a biologically effective amount.

It will be apparent to the skilled addressee that the method of producing the composition may also incorporate further steps and incorporating or mixing the composition with additional components as described above.

In accordance with yet another aspect of the present invention, there is provided a method of treating an individual with elevated cholesterol serum levels, heart disease, diabetes or obesity by administering an effective amount of at least one of the strains selected from *Lactobacillus plantarum* 2828 (ECGC 13110403); *Lactobacillus plantarum* 2830 (ECGC 13110402); and *Lactobacillus plantarum* 2691 (ECGC 13110401) and *Lactobacillus acidophilus* ATCC 43121 or mutant strains thereof and a cholesterol modifying agent.

A method may comprise administering two or more strains selected from *Lactobacillus plantarum* 2828 (ECGC 13110403); *Lactobacillus plantarum* 2830 (ECGC 13110402); and *Lactobacillus plantarum* 2691 (ECGC 13110401) and *Lactobacillus acidophilus* ATCC 43121 or mutant strains thereof.

It will be apparent to the skilled addressee that a number of the features of the composition listed in respect to the earlier aspects of the invention will of course be interchangeable with the method and can form a composition which is adminsitered to an individual.

DETAILED DESCRIPTION OF THE INVENTION

Embodiments of the present invention will now be described, by way of example only in which:

FIG. 2A is a graph of bacterial count over time using 5% lactose as a growth medium for *L. plantarum* in Experiment 1;

FIG. 2B is a graph of bacterial count over time using 5% lactose as a growth medium for *L. casei* in Experiment 1;

FIG. 2C is a graph of bacterial count over time using 5% lactose as a growth medium for *L. salivarius* in Experiment 1;

FIG. 2D is a graph of bacterial count over time using 5% lactose as a growth medium for *L. delbrueckii* in Experiment 1;

FIG. 8 is a pie chart showing the diverse range of *Lactobacilli* strains which underwent high throughput screening;

FIG. 10 is a bar chart showing the results of the 24 strains shown in FIG. 5 after normalizing cholesterol assimilation to the optical density;

EXPERIMENT 1

Figure 1A:
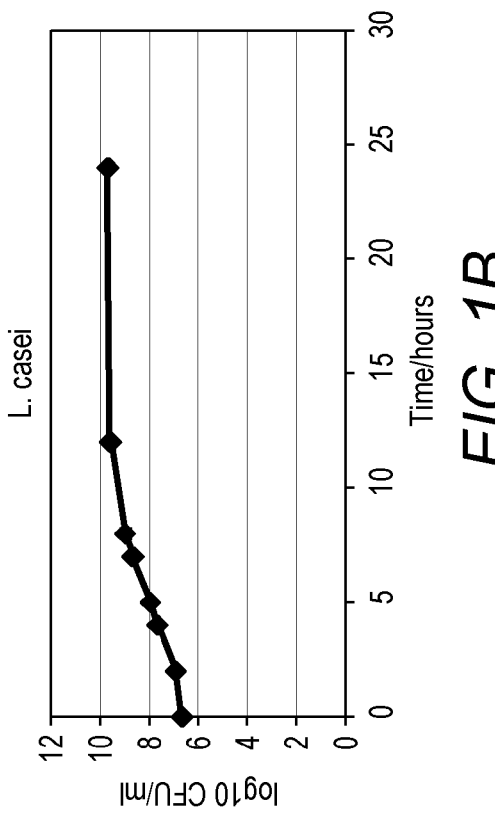
FIG. 1A is a graph of bacterial count over time using 0.1% lactose as a growth medium for *L. plantarum* in Experiment 1.
Figure 1B:
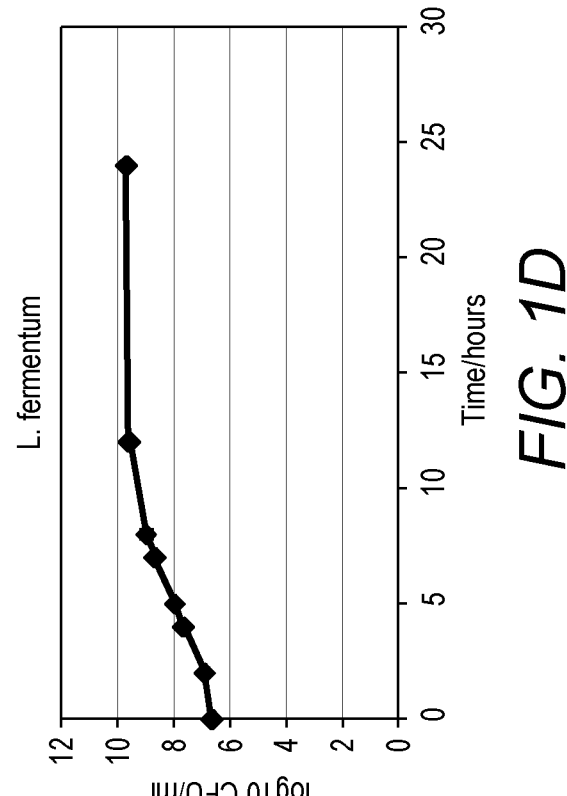
FIG. 1B is a graph of bacterial count over time using 0.1% lactose as a growth medium for *L. casei* in Experiment 1.
Figure 1C:
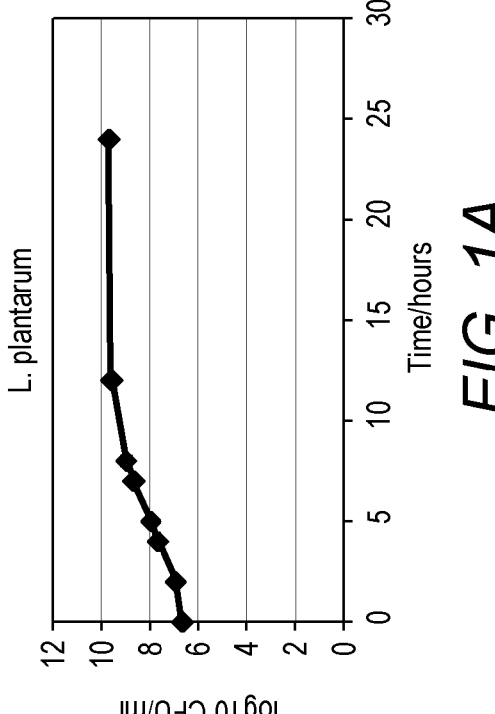
FIG. 1D is a graph of bacterial count over time using 0.1% lactose as a growth medium for *L. fermentum* in Experiment 1.
FIG. 1E is a graph of bacterial count over time using 0.1% lactose as a growth medium for *L. rhanmosus* in Experiment 1.
FIG. 1F is a graph of bacterial count over time using 0.1% lactose as a growth medium for *L. delbrueckii* in Experiment 1.
Figure 1D:
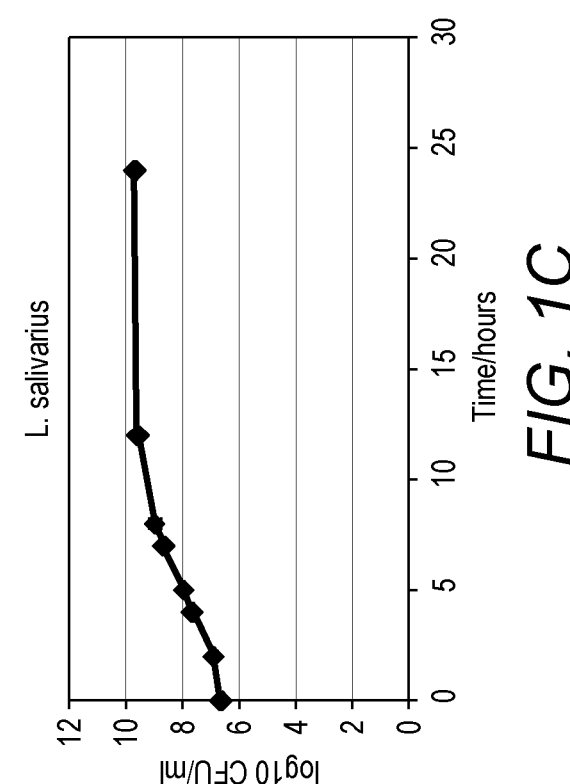
Figure 1F:
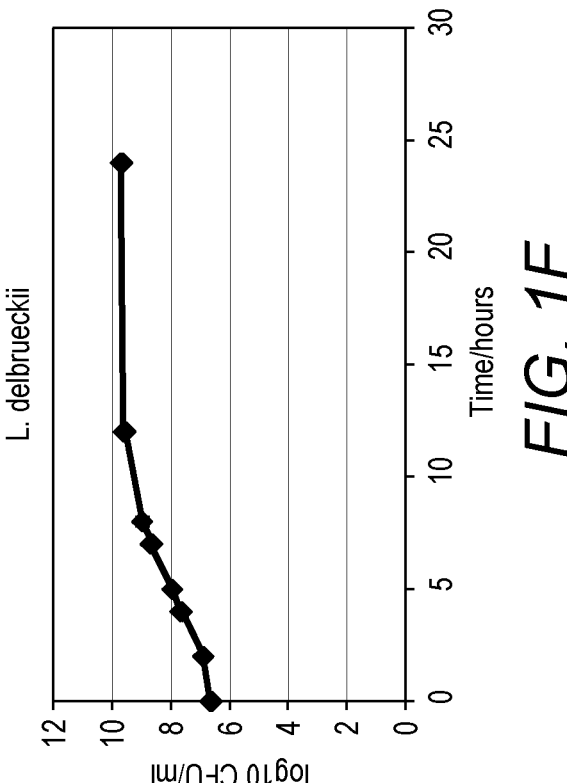
Figure 1E:
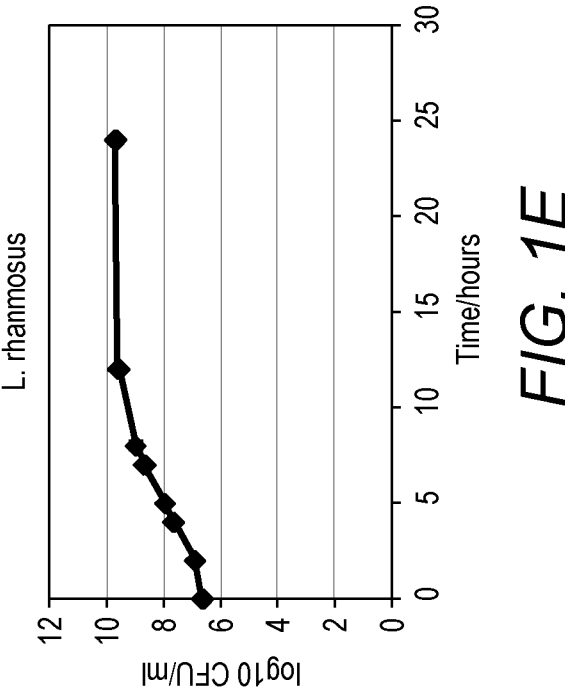
Figure 2F:
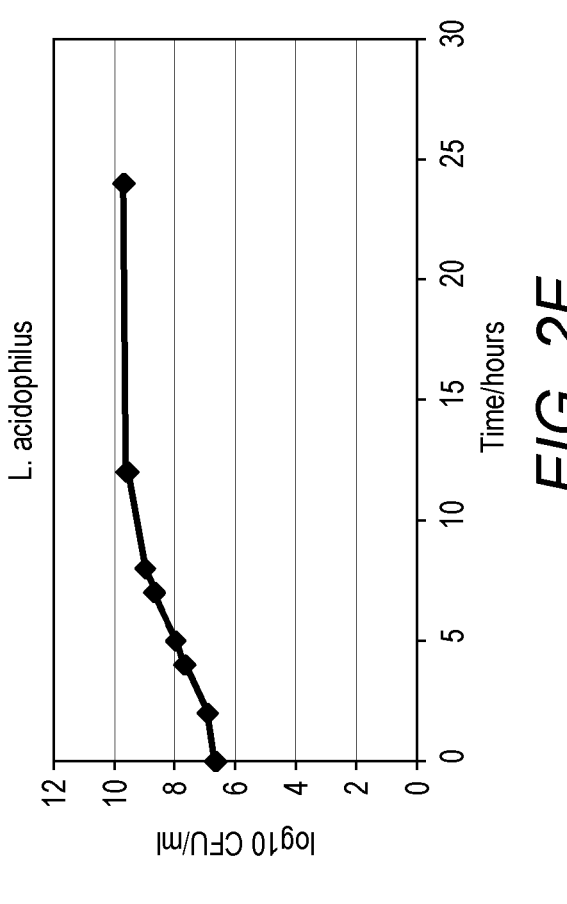
FIG. 2F is a graph of bacterial count over time using 5% lactose as a growth medium for *L. acidophilus* in Experiment 1.
Figure 2E:
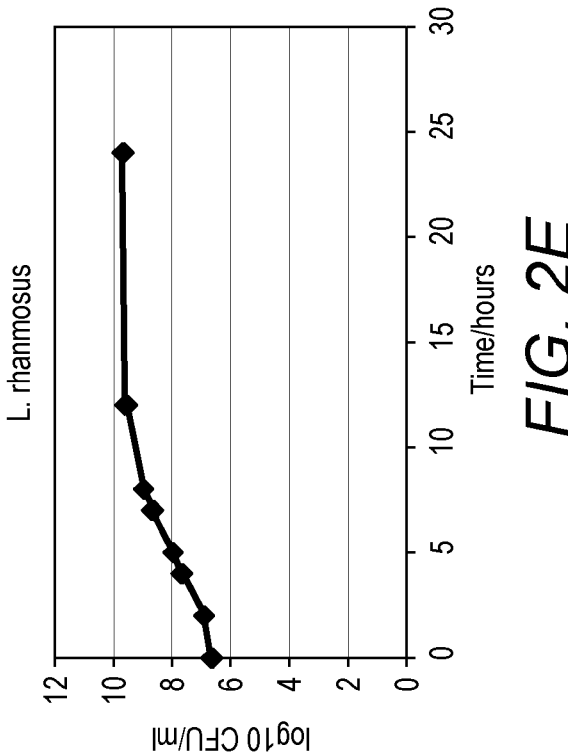
FIG. 2E is a graph of bacterial count over time using 5% lactose as a growth medium for *L. rhanmosus* in Experiment 1.
Figure 2G:
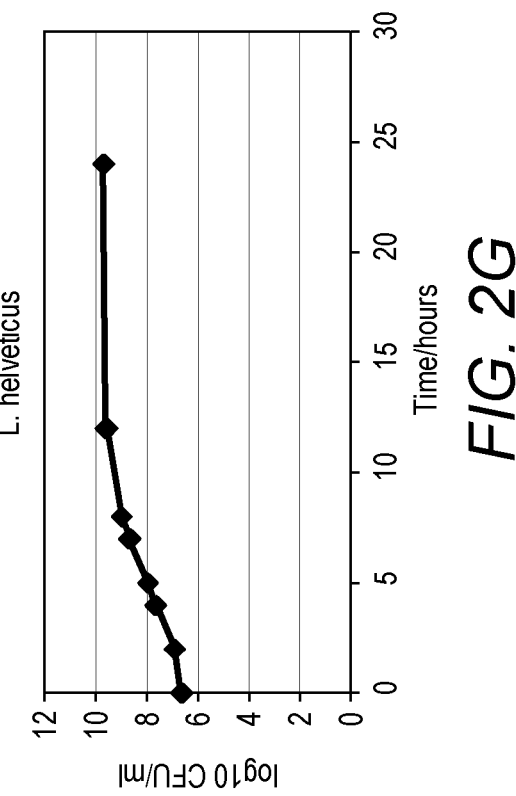
FIG. 2G is a graph of bacterial count over time using 5% lactose as a growth medium for *L. helveticus* in Experiment 1.

The basis of these experiments were to reversibly use β-galactosidases in microorganisms so as to produce a novel GOS. Ordinarily, β-galactosidases would digest lactose. However, by changing the reaction conditions, in terms of substrate and temperature, the enzyme acts reversibly and generates an oligosaccharide version of the lactose (GOS).

*Lactobacilli* are more frequently used as probiotics than are bifidobacteria, yet no prebiotic selective to lactobacilli exists. As these probiotics also harbour β-galactosidase activity, the experiments induced the production of GOS which was specific to these probiotics. The metabolism of prebiotics like GOS are species specific (as evidenced by Bi-Immuno and Bifido bacteria), so a *Lactobacilli* GOS has the potentially enhance the growth, survivability, and health benefits of lactobacilli.

The experiments undertaken were as follows:

1. Assemble and test a range of probiotic lactobacilli for their capacity to generate GOS and measuring β-galactosidase activities;
2. Generate a prebiotic GOS using the reverse enzyme procedure;
3. Scale up of the novel molecule to allow in vitro testing;
4. Compare survival and growth of lactobacilli in the absence and presence of the prebiotic in a series of 'gut model' experiments that test the probiotics and synbiotics;
5. Assess the possibility for using GOS as encapsulation material for the lactobacilli; and
6. Test delivery properties of the encapsulation material.

The bacterial strains initially investigated during the first stage of the experiments are shown below in Table 1:

TABLE 1

| Strain | Number | Origin |
|---|---|---|
| *Lactobacillus acidophilus* | NCIMB 30184 | Human |
| *Lactobacillus rhamnosus* | NCIMB 30188 | Human |
| *Lactobacillus plantarum* | NCIMB 30187 | Pickled cabbage |
| *Lactobacillus delbrueckii* ssp. *bulgaricus* | NCIMB 30186 | Yogurt |
| *Lactobacillus casei* | NCIMB 30185 | Cheese |
| *Lactobacillus salivarius* ssp. *salivarius* | NCIMB 30225 | Human |

TABLE 1-continued

| Strain | Number | Origin |
|---|---|---|
| *Lactobacillus fermentum* | NCIMB 30226 | Dairy |
| *Lacobacillus helveticus* | NCIMB 30224 | Dairy |
| *Lactobacillus fermentum* | ATCC11976 | Human |
| *Lactobacillus salivarius* | ATCC 11741 | Human |

Bacterial growth curve determination was undertaken by sampling cultures at 0 h, 3 h, 5 h, 8 and 24 h intervals using a 100 μL of dilution series of culture in 900 μL PBS. 20 μL of each series was spread onto a jar and with a negative control and growth assessed.

Bacterial count of several of the strains was assessed by using 0.1% lactose as the growth medium. FIGS. 1A-1F show that bacterial count over time using 0.1% lactose as a growth medium for *L. plantarum*, *L. casei*, *L. salivarius*, *L. fermentum*, *L. rhanmosus*, and *L. delbrueckii* all resulted in a steady growth curve from approximately 6.5 log 10 CFU/ml to just over 9.5 log 10 CFU/ml at around 13 hours and growth tailed off as it did not increase by 25 hours.

Bacterial count of several of the strains was assessed by using 5% lactose as the growth medium. FIGS. 2A-2G show the bacterial count over time using 5% lactose as a growth medium for *L. plantarum*, *L. casei*, *L. salivarius*, *L. delbrueckii*, *L. rhanmosus*, *L. acidophilus* and *L. helveticus*. Again, all resulted in a steady growth curve from approximately 6.5 log 10 CFU/ml to just over 9.5 log 10 CFU/ml at around 13 hours and growth was then flat as it did not increase by 25 hours.

Cholesterol was then included in the culture medium of the bacterial strains and each strain tested for quantity of cholesterol after incubation.

The cholesterol assay used relies on the following formula:

$$\% \text{ cholesterol} \times \text{dry weight (g)}^{-1} = (B - T/B \times 100)/W$$

Where B=cholesterol content in the uninoculated control mg/l$^{-1}$, T=cholesterol in culture medium mg/l$^{-1}$ and W=cells (dry weight g after 12 h of inc).

The pellet weight of the culture was measured independently of the supernanent and the spent broth (evaporated residues) also measured. The cholesterol assay was run in triplicate in several runs.

Figure 3:
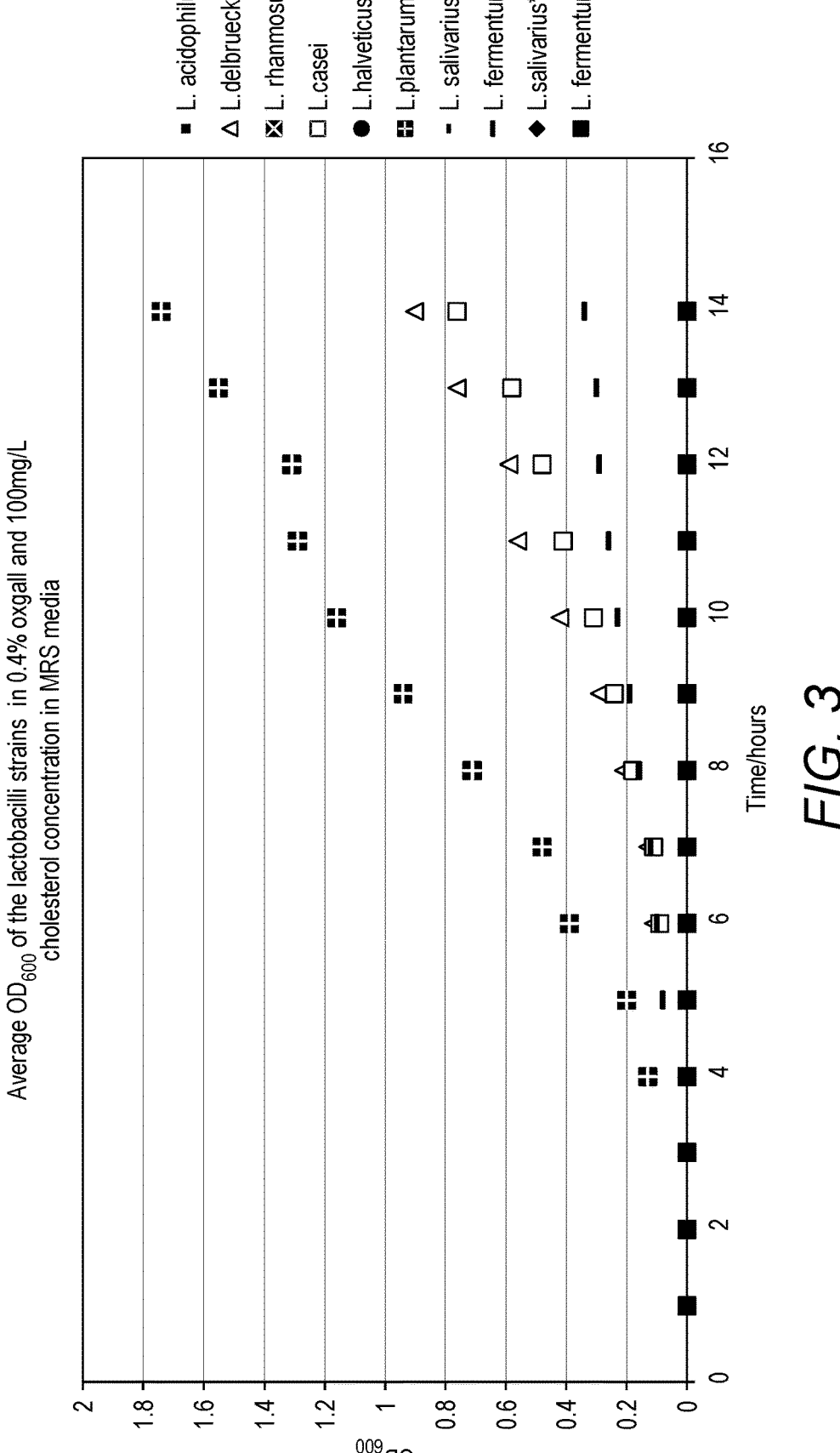
FIG. 3 is a graph showing the results of different bacterial strains over 14 hours ($OD_{600}$ measured every hour) in 0.4% oxgall and 100 mg/L cholesterol concentration in MRS media in Experiment 1.

FIG. 3 shows the growth of different bacterial strains over 14 hours (OD$_{600}$ measured every hour) in 0.4% oxgall and 100 mg/L cholesterol concentration in MRS media and shows that some bacterial strains were much more effective at growing in this media. *L. Planatarum* showed the best growth profile, followed by *L. delbrueckii*, *L. casei* and *L. fermentum*.

FIG. 3 shows the growth of different bacterial strains over 12 hours (OD$_{600}$ measured every hour) in 0.4% oxgall and 100 mg/L cholesterol concentration in MRS media and shows that some bacterial strains were much more effective at growing in this media. *L. planatarum* showed the best growth profile, followed by *L. delbrueckii*, *L. casei* and *L. fermentum*.

Figure 4:
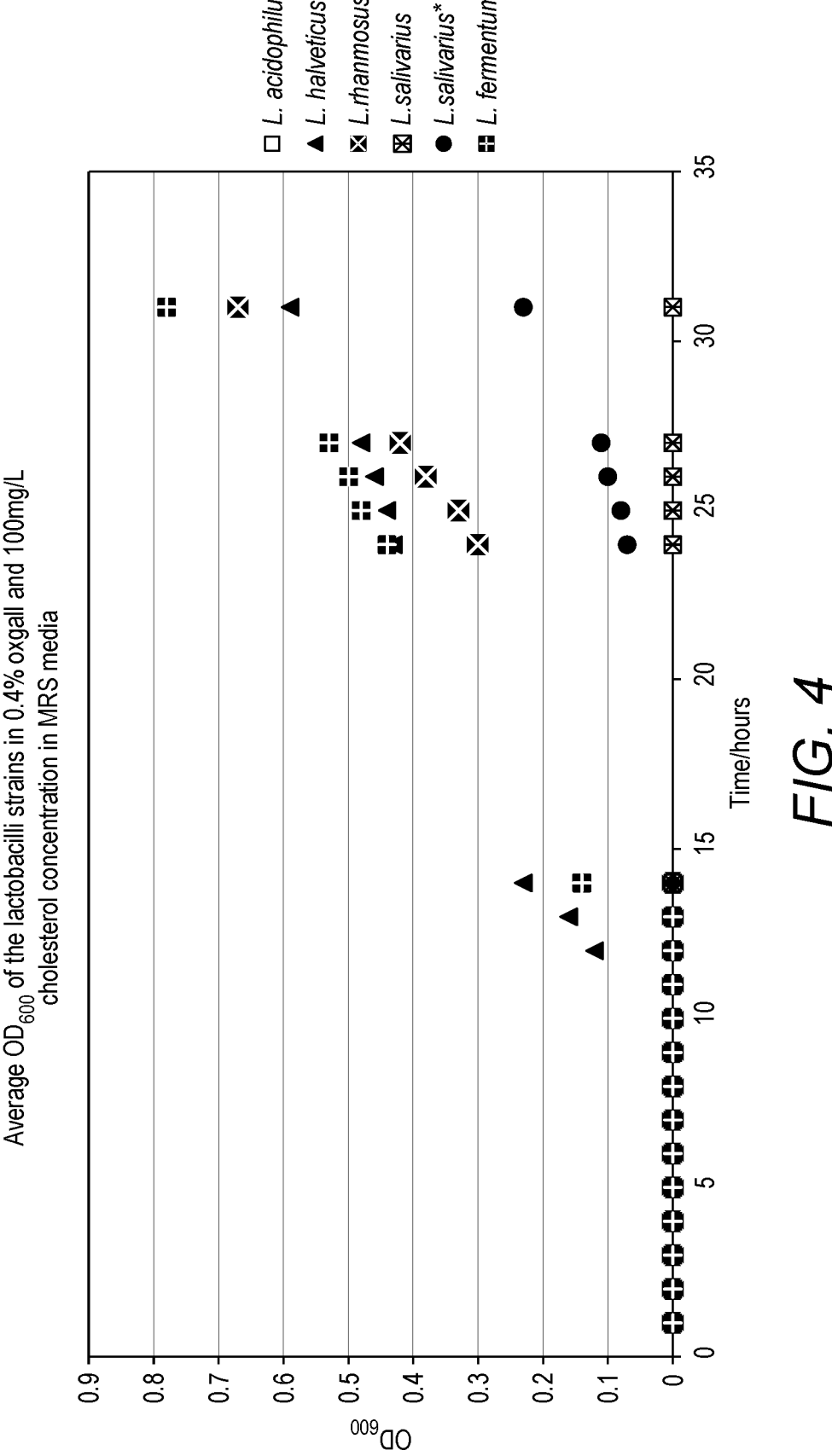
FIG. 4 is a graph showing the results of different bacterial strains over 2 days prior to testing ($OD_{600}$ measured every hour) in 0.4% oxgall and 100 mg/L cholesterol concentration in MRS media in Experiment 1.

FIG. 4 is a graph showing the results of different bacterial strains over 2 days prior to testing (OD$_{600}$ measured every hour) in 0.4% oxgall and 100 mg/L cholesterol concentration in MRS media. *L. fermentum* showed the best growth profile, followed by *L. rhanmosus*, *L. halveticus*, *L. halveticus* and *L. salivarius*.

Direct plate assay tests were then conducted on the strains to further measure cholesterol activity. Resting cell Bile Salt Hydrolase (BSH) activity was measured to assess the release of amino acids from hydrolysis of conjugated bile acids. Bile salt deconjugation (based upon the release of free cholic acid) was measured and finally co-precipitation of cholesterol with deconjugated bile assessed. Table 2 below shows the results of the direct plate assay.

TABLE 2

| Bacteria | $1^{st}$ run | $2^{nd}$ run | $3^{rd}$ run |
|---|---|---|---|
| L. casei | Y | Y | Y |
| L. delbrueckii | Y | Y | Y |
| L. acidophilus | Y | Y | Y |
| L. fermentum | X | Y | Y |
| L. salivarius | X | X | X |
| L. halveticus | Y | X | X |
| L. rhamnosus | X | X | X |
| L. plantarum | X | Y | Y |
| L. salivarius* | X | X | X |
| L. fermentum* | X | X | Y |

It can be seen that *L. casei*, *L. delbrueckii* and *L. acidophilus* all had reliable BSH activity. However, *L. fermentum* and *L. plantarum* also had successful growths (2 out of 3 runs) and *L. plantarum* had previously proved particularly effective at growing on 0.4% oxgall and 100 mg/L cholesterol as illustrated in FIGS. 3 and 4.

By comparing the results of the strains being able to grow in media containing cholesterol and those strains having BSH activity *L. casei, L. delbrueckii, L. fermentum* and *L. plantarum* appeared to be suitable candidates for producing and identifying a specific prebiotic GOS.

The GOS prebiotic generated by a specific strain has optimised metabolism not just to produce the GOS, but also to metabolise it (as it is generated from a reverse enzyme procedure). The GOS can therefore be incorporated with the probiotic into a synbiotic that would create a highly selective environment for the probiotic. As a probiotic can have a specific health benefits then a synbiotic formula which is tailored to a specific health benefit can be generated.

EXPERIMENT 2

In parallel to Experiment 1, an initial high throughput screening (HTS) trial of 718 strains of *Lactobacilli* was conducted to assess the resistance to different types of bile salts. Further experiments were then conducted to investigate bile precipitation in 286 resistant strains in order to establish bile salt hydrolase activity.

The strains tested were: *Lactobacilli acidophilus, Lactobacilli helveticus, Lactobacilli alimentarius, Lactobacilli brevis, Lactobacilli buchneri, Lactobacilli casei* (including subspecies: *rhamnosus, casei, tolerans, pseudoplantarum, paracasei, alactotsus* and *rhamnosus*), *Lactobacilli crispatus, Lactobacilli curvatus* (including subspecies: *curvatus*), *Lactobacilli delbrueckii* (including subspecies: *bulgaricus* and *lactis*), *Lactobacilli* fermentum, *Lactobacilli* panis, *Lactobacilli paracasei* (including subspecies: *paracasei*), *Lactobacilli* pentosus, *Lactobacilli* planatarum, *Lactobacilli* rhamnosus, *Lactobacilli* sakei, *Lactobacilli salivarius* (including subspecies: *salivarius*).

Strains were grown overnight in MRS at 37° C. Of these cultures glycerol stocks were made and stored at −80° C. A microtiterplate was inoculated and all strains were placed in quadriplicate into masterplates.

The bile salts used in these experiments were purchased from Sigma® and were as follows: Sodium glycodeoxycholate (GDCA) (Sigma product number G3258, CAS: 16409-34-0); sodium taurodeoxycholate hydrate (TDCA) (Sigma product number T0875, CAS: 207737-97-1) and Bile bovine (Oxgal) (Sigma product number B3883, CAS: 8008-63-7). The concentrations of the bile salts used in the experiments were as follows: 0.5% GDCA; 0.5% TDCA; 0.5% oxgal; and 2.0% oxgal. In vitro data using glycodeoxycholate is believed to be more likely to reflect the likelihood of product efficacy as it more closely mimics the in vivo human environment.

Overnight cultures were grown in 96 well plates in MRSA at 37° C. Then 5 µl of the cultures spotted into wells containing 150 µl MRSA agar with added bile salts in 96 well plates and incubated for 48 hours under aerobic/anaerobic conditions. pH conditions were monitored so as to ensure proper growth of the strains.

The results showed that certain strains do grow on the MRSA plates under both anaerobic and aerobic conditions. Table 3 below shows all of the positive results from the initial HTS where a particular strain is capable of growing (assessed by measurement of $OD_{600}$) on a range of bile salts under anaerobic conditions:

TABLE 3

| Lactobacilli species/strain | Average of 0.5% TDCA-24 h | Average of 0.5% TDCA-72 h | Average of 0.5% GDCA-24 h | Average of 0.5% GDCA-72 h | Average of 0.5% Oxgal-24 h | Average of 0.5% Oxgal-72 h | Average of 2.0% Oxgal-24 h | Average of 2.0% Oxgal-72 h |
|---|---|---|---|---|---|---|---|---|
| Lactobacillus brevis | Y | Y | Y | Y | Y | Y | Y | Y |
| 293 | Y | Y | Y | Y | Y | Y | Y | Y |
| 306 | Y | Y | Y | Y | Y | Y | Y | Y |
| 1692 | Y | Y | Y | Y | Y | Y | Y | Y |
| Lactobacillus casei | Y | Y | Y | Y | Y | Y | Y | Y |
| 262 | Y | Y | Y | Y | Y | Y | Y | Y |
| 1694 | Y | Y | Y | Y | Y | Y | Y | Y |
| Lactobacillus plantarum | Y | Y | Y | Y | Y | Y | Y | Y |
| 1683 | Y | Y | Y | Y | Y | Y | Y | Y |
| 2258 | Y | Y | Y | Y | Y | Y | Y | Y |
| 2471 | Y | Y | Y | Y | Y | Y | Y | Y |
| 2472 | Y | Y | Y | Y | Y | Y | Y | Y |
| 2475 | Y | Y | Y | Y | Y | Y | Y | Y |
| 2478 | Y | Y | Y | Y | Y | Y | Y | Y |
| 2480 | Y | Y | Y | Y | Y | Y | Y | Y |
| 2481 | Y | Y | Y | Y | Y | Y | Y | Y |
| 2487 | Y | Y | Y | Y | Y | Y | Y | Y |
| 2490 | Y | Y | Y | Y | Y | Y | Y | Y |
| 2491 | Y | Y | Y | Y | Y | Y | Y | Y |

TABLE 3-continued

| Lactobacilli species/strain | Average of 0.5% TDCA-24 h | Average of 0.5% TDCA-72 h | Average of 0.5% GDCA-24 h | Average of 0.5% GDCA-72 h | Average of 0.5% Oxgal-24 h | Average of 0.5% Oxgal-72 h | Average of 2.0% Oxgal-24 h | Average of 2.0% Oxgal-72 h |
|---|---|---|---|---|---|---|---|---|
| 2492 | Y | Y | Y | Y | Y | Y | Y | Y |
| 2534 | Y | Y | Y | Y | Y | Y | Y | Y |
| 2536 | Y | Y | Y | Y | Y | Y | Y | Y |
| 2819 | Y | Y | Y | Y | Y | Y | Y | Y |
| 2826 | Y | Y | Y | Y | Y | Y | Y | Y |
| 2828 | Y | Y | Y | Y | Y | Y | Y | Y |
| 2830 | Y | Y | Y | Y | Y | Y | Y | Y |
| 2831 | Y | Y | Y | Y | Y | Y | Y | Y |
| 2832 | Y | Y | Y | Y | Y | Y | Y | Y |
| 4038 | Y | Y | Y | Y | Y | Y | Y | Y |
| 299 (1837) | Y | Y | Y | Y | Y | Y | Y | Y |
| AbBio | Y | Y | Y | Y | Y | Y | Y | Y |
| WCFS1 (1836) | Y | Y | Y | Y | Y | Y | Y | Y |
| *Lactobacillus salivarius* ssp. *Salivarius* | Y | Y | Y | Y | Y | Y | Y | Y |
| NCIMB 30225 | Y | Y | Y | Y | Y | Y | Y | Y |

Figure 5:
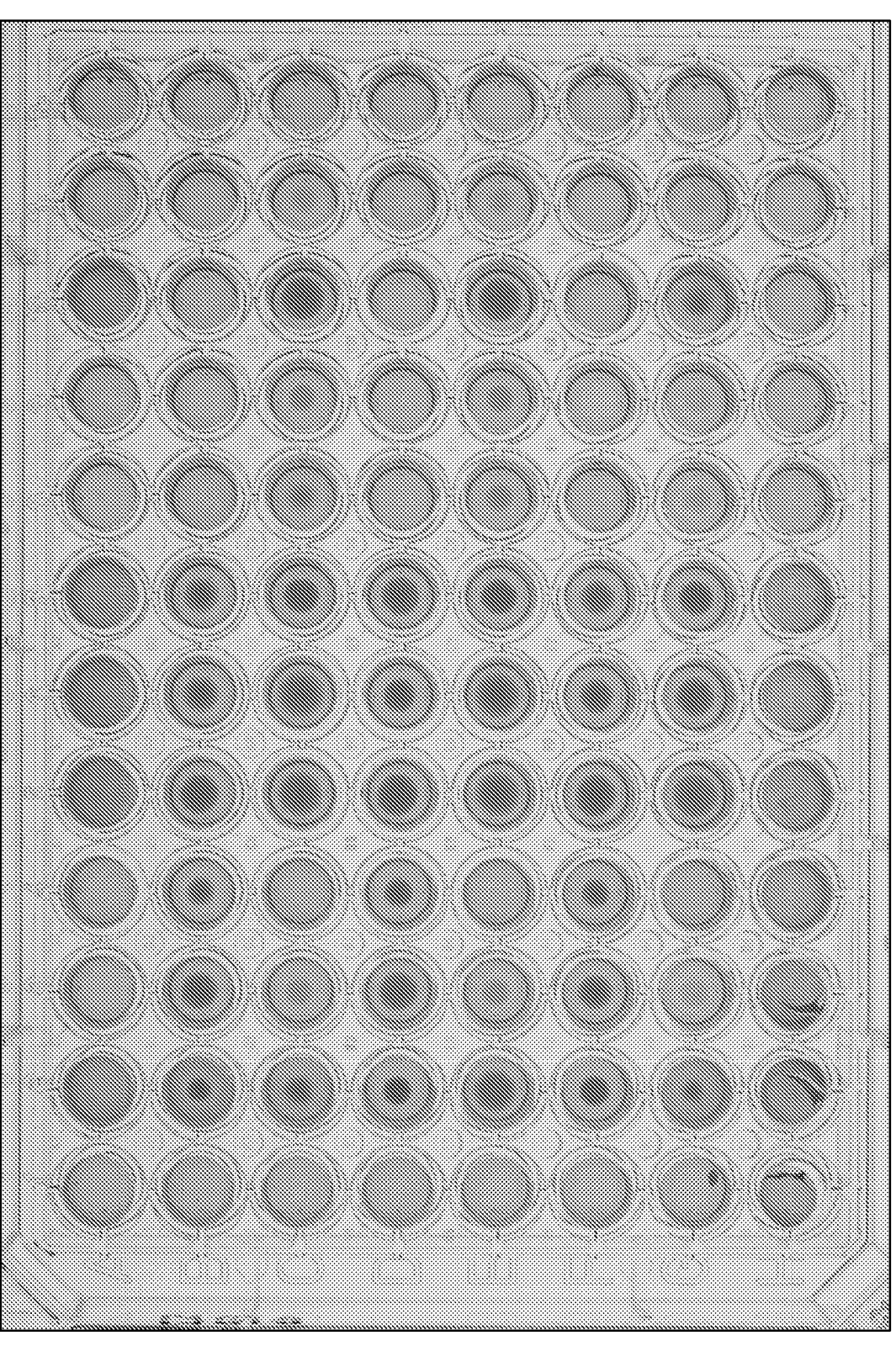
FIG. 5 is a photograph of *Lactobacilli* strains gown in MRSA on a 96 well plate under aerobic conditions in Experiment 2.
Figure 6:
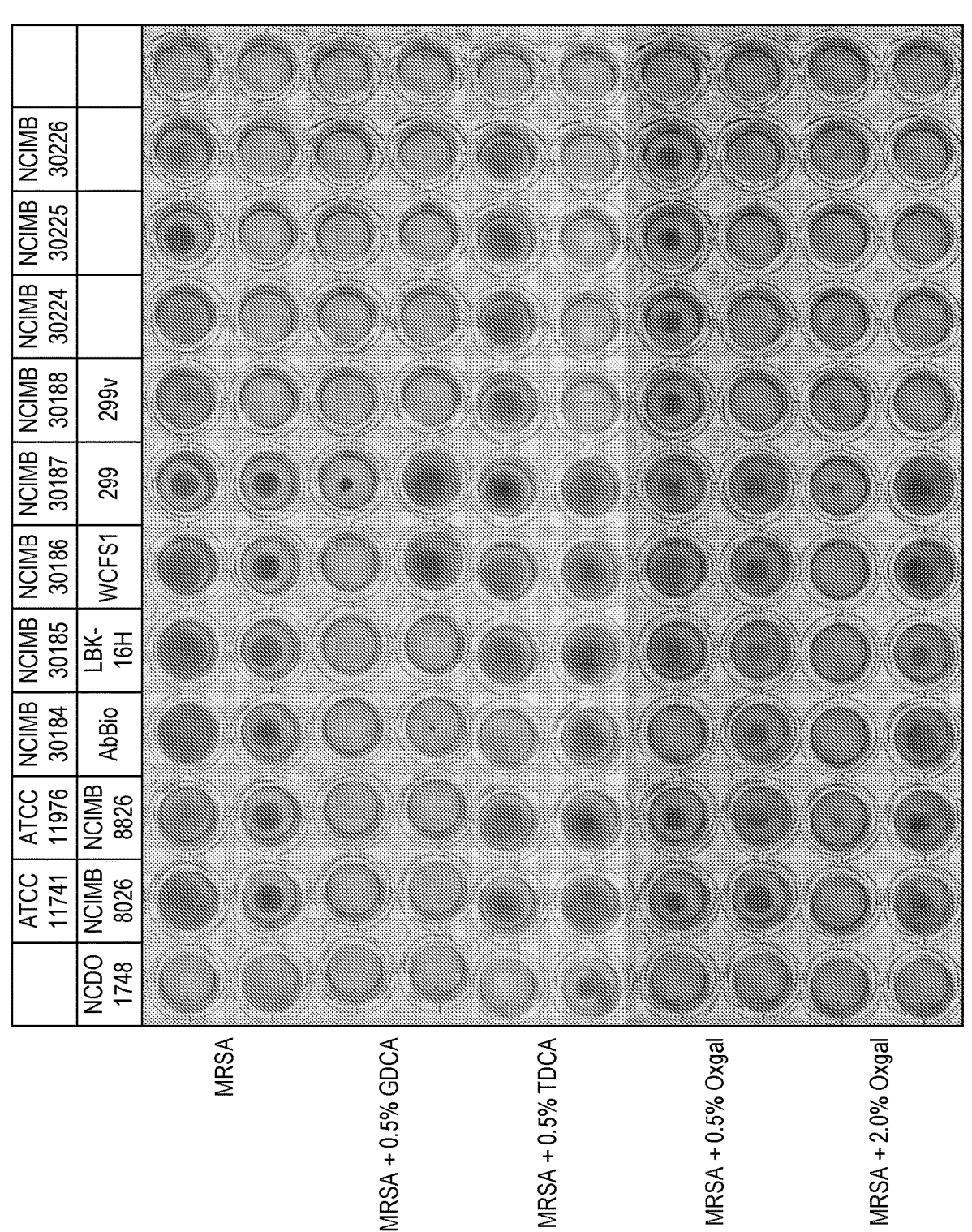
FIG. 6 is a photograph of *Lactobacilli* strains grown on a 96 well plate under anaerobic conditions, the strains being grown in MRSA only (control), MRSA+0.5% GDCA, MRSA+0.5% TDCA, MRSA+0.5% Oxgal; and MRSA+2% Oxgal in Experiment 2.
Figure 7:
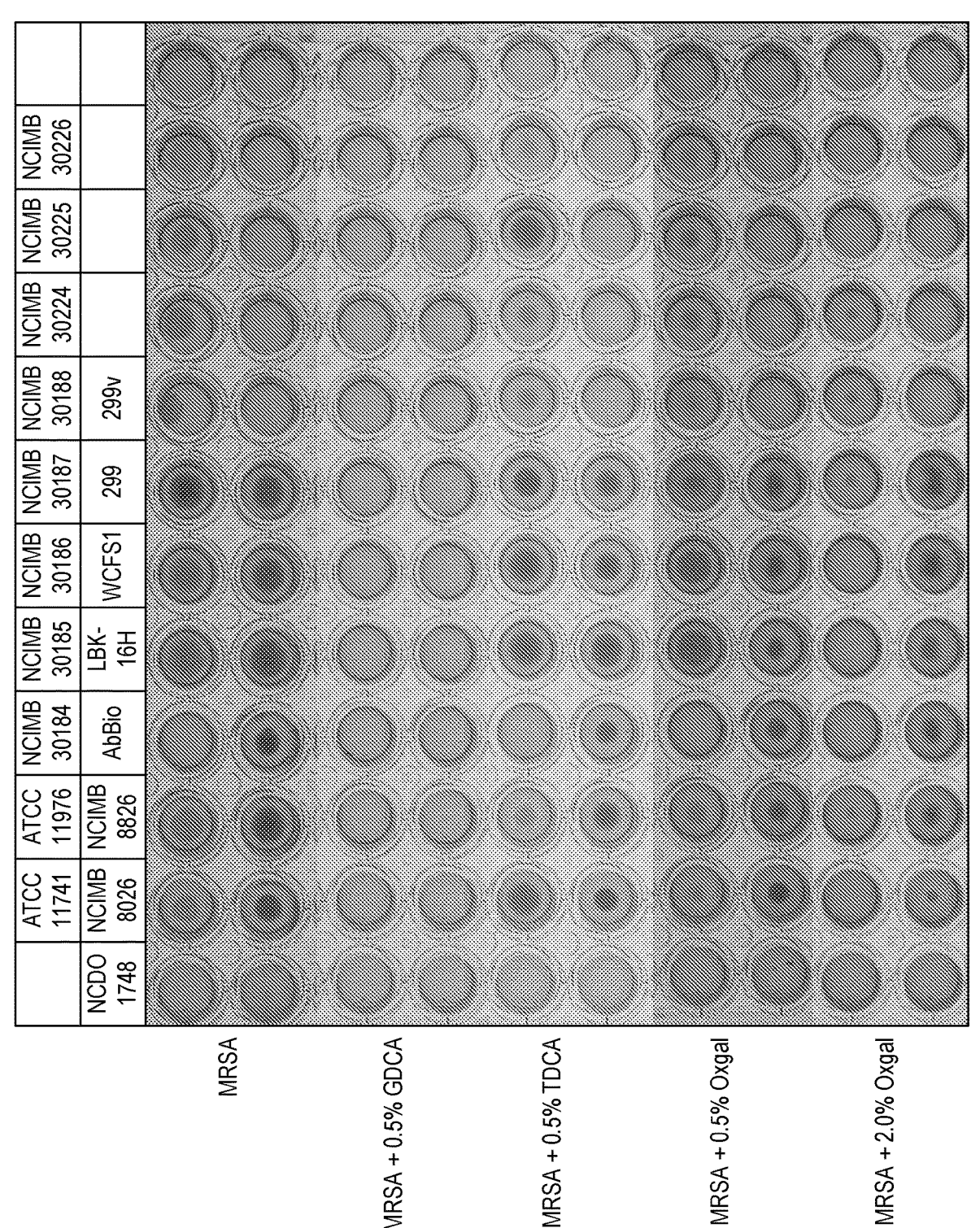
FIG. 7 is a photograph of *Lactobacilli* strains grown on a 96 well plate under aerobic conditions, the strains being grown in MRSA only (control), MRSA+0.5% GDCA, MRSA+0.5% TDCA, MRSA+0.5% Oxgal; and MRSA+2% Oxgal in Experiment 2.

FIG. 5 illustrates that many strains grow well in MRSA under aerobic conditions. As shown in FIG. 7, GDCA inhibits growth of the strains in all cases under aerobic conditions but as shown in FIG. 6 under anaerobic conditions some strains do grow in GDCA. 2.0% Oxgal was found to inhibit the growth of some strains in both aerobic and anaerobic conditions. The plates in FIGS. 6 and 7 show good growth for the following strains: (*Lactobacillus plantarum* NCIMB 8026, *Lactobacillus fermentum* ATCC 11976, *Lactobacillus plantarum* NCIMB 8826, *Lactobacillus plantarum* AbBio, *Lactobacillus helveticus* LBK-16H, *Lactobacillus plantarum* WCF51 (1836), *Lactobacillus plantarum* NCIMB 30187, *Lactobacillus plantarum* 299 (1837). When these results are compared with the growth data of comparative strains grown in a medium containing 100 mg/L cholesterol in Experiment 1 (and illustrated in FIGS. 3 and 4) it appears that *Lactobacillus plantarum* and *Lactobacillus fermentum* have excellent growth in the presence of cholesterol and are resistive to bile salts and have bile salt hydrolase activity.

Table 4 below shows a brief summary of the growth results:

TABLE 4

| Media | Strains grown at 20/72 hours |
|---|---|
| 0.5% TDCA | 163/208 |
| 0.5% GDCA | 38/45 |

TABLE 4-continued

| Media | Strains grown at 20/72 hours |
|---|---|
| 0.5% Oxgal | 116/160 |
| 2.0% Oxgal | 84/103 |

A total of 41 strains were found to grow in the presence of all three bile salts present at 0.5%.

Bile salt hydrolase activity in resistant strains was then assessed by spotting 5 µl into "PCR tube plate" (150 µl of agar in a thin walled microcentrifuge tubes). These tube plates were grown under the same conditions as the 96 well plates (MRS+0.5% TDCA, MRS+0.5% GDCA, MRS+0.5% oxgal, MRS+2.0% oxgal, MRS without bile (control)).

The plates were incubated anaerobically at 37° and bile precipitation (related to bile salt hydrolase activity) was assessed after 24 and 48 h using the following scoring system: Record growth as + or − for BSH activity. The positives were then selected for subsequent streaking onto MRS plates containing 0.5% oxgal.

After 72 hours, positive strains had been identified. The positive cultures only showed precipitation in GDCA and TDCA.

FIG. 8 shows the range of strains used in the initial high throughput screening assay.

After narrowing down the number of strains to 24 based on earler BSH activity, further screening of the cholesterol assimilation in MRS medium supplemented with 0.4% was conducted.

Table 3 below shows the results of the selected strains and their average % cholesterol reduction.

TABLE 3

| Strain | Biological replicate 1 OD after 24 hours growth | Biological replicate 2 OD after 24 hours growth | Biological replicate 1 Cholesterol in mg/l | Biological replicate 2 Cholesterol in mg/l | Biological replicate 1 % cholesterol reduction | Biological replicate 2 % cholesterol reduction | Average % cholesterol reduction |
|---|---|---|---|---|---|---|---|
| 306 | 1.58 | 1.45 | 21.0 | 19.6 | 5.7 | 12.0 | 8.9 |
| 2490 | 1.31 | 1.28 | 19.1 | 21.5 | 14.4 | 3.7 | 9.1 |
| 2471 | 1.55 | 1.53 | 19.7 | 19.4 | 11.4 | 13.1 | 12.2 |
| 2475 | 0.72 | 0.75 | 19.1 | 20.0 | 14.4 | 10.4 | 12.4 |
| 2478 | 1.56 | 1.5 | 19.0 | 19.2 | 14.7 | 14.0 | 14.3 |
| 2480 | 1.2 | 1.04 | 19.3 | 18.3 | 13.4 | 18.0 | 15.7 |
| 1708 | 2.2 | 1.9 | 18.1 | 19.4 | 18.7 | 13.1 | 15.9 |
| 2472 | 1.66 | 1.95 | 19.0 | 17.6 | 14.9 | 21.0 | 17.9 |
| 2260 | 3.52 | 3.62 | 11.5 | 11.3 | 48.2 | 49.1 | 48.7 |

TABLE 3-continued

| Strain | Biological replicate 1 OD after 24 hours growth | Biological replicate 2 OD after 24 hours growth | Biological replicate 1 Cholesterol in mg/l | Biological replicate 2 Cholesterol in mg/l | Biological replicate 1 % cholesterol reduction | Biological replicate 2 % cholesterol reduction | Average % cholesterol reduction |
|---|---|---|---|---|---|---|---|
| ATCC 11976 | 1.37 | 1.44 | 2.63 | 6.77 | 71.5 | 26.8 | 49.2 |
| 293 | 3.54 | 3.27 | 10.8 | 11.4 | 51.7 | 48.7 | 50.2 |
| 1836 | 3.61 | 3.75 | 9.7 | 12.3 | 56.3 | 44.6 | 50.5 |
| 1837 | 3.6 | 3.72 | 10.1 | 10.0 | 54.4 | 54.9 | 54.7 |
| 2481ˆ | 1.45 | 1.42 | 1.0 | 18.4 | 95.4 | 17.3 | 56.3 |
| 1683 | 4.28 | 3.92 | 10.6 | 8.6 | 52.4 | 61.3 | 56.9 |
| 2535 | 2.65 | 2.62 | 9.1 | 8.1 | 59.3 | 63.5 | 61.4 |
| ATCC 11741 | 1.24 | 1.33 | 3.43 | 3.50 | 62.9 | 62.1 | 62.5 |
| 2826 | 3.28 | 4.36 | 7.3 | 6.8 | 67.0 | 69.4 | 68.2 |
| 2691 | 3.12 | 2.68 | 7.1 | 5.7 | 68.2 | 74.4 | 71.3 |
| ATCC 43121 | 3.15 | 4.52 | 6.4 | 4.4 | 71.4 | 80.1 | 75.7 |
| 2831 | 3.75 | 3.81 | 4.5 | 5.5 | 79.6 | 75.4 | 77.5 |
| 2830 | 3.22 | 2.84 | 5.3 | 4.5 | 76.1 | 79.7 | 77.9 |
| 2828 | 3.4 | 3.02 | na** | 4.0 | | 82.2 | 82.2 |
| NCIMB30187 | 2.75 | 2.58 | 3.5 | 4.3 | 84.4 | 80.8 | 82.6 |

Figure 9:
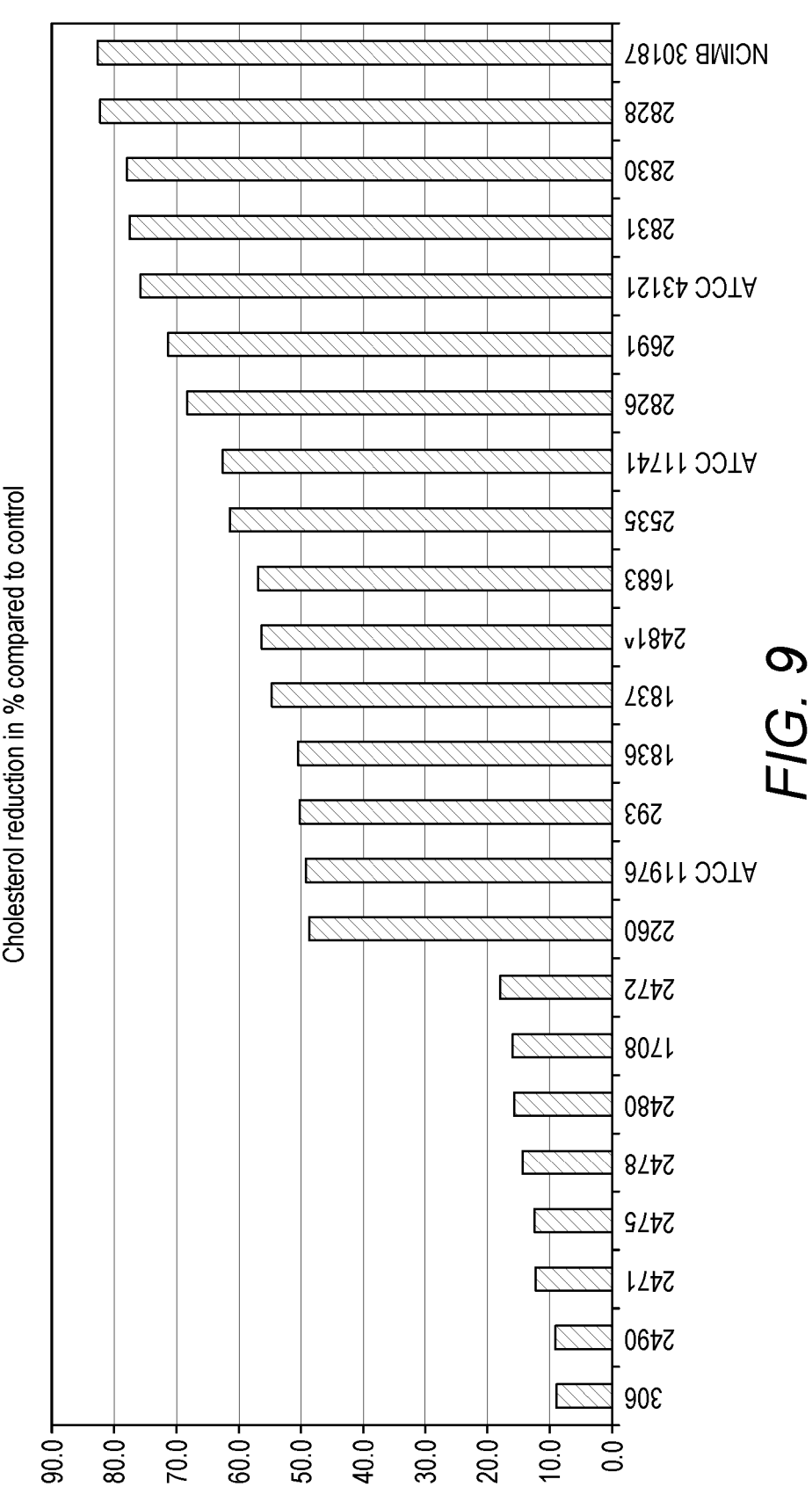
FIG. 9 is a bar chart showing the results of the 24 strains which were identified for further analysis of their cholesterol reducing ability.

FIG. 9 shows the results of the table in a bar chart and illustrates that there is a big difference between the first 8 strains compared to the rest of the strains.

Figure 10:
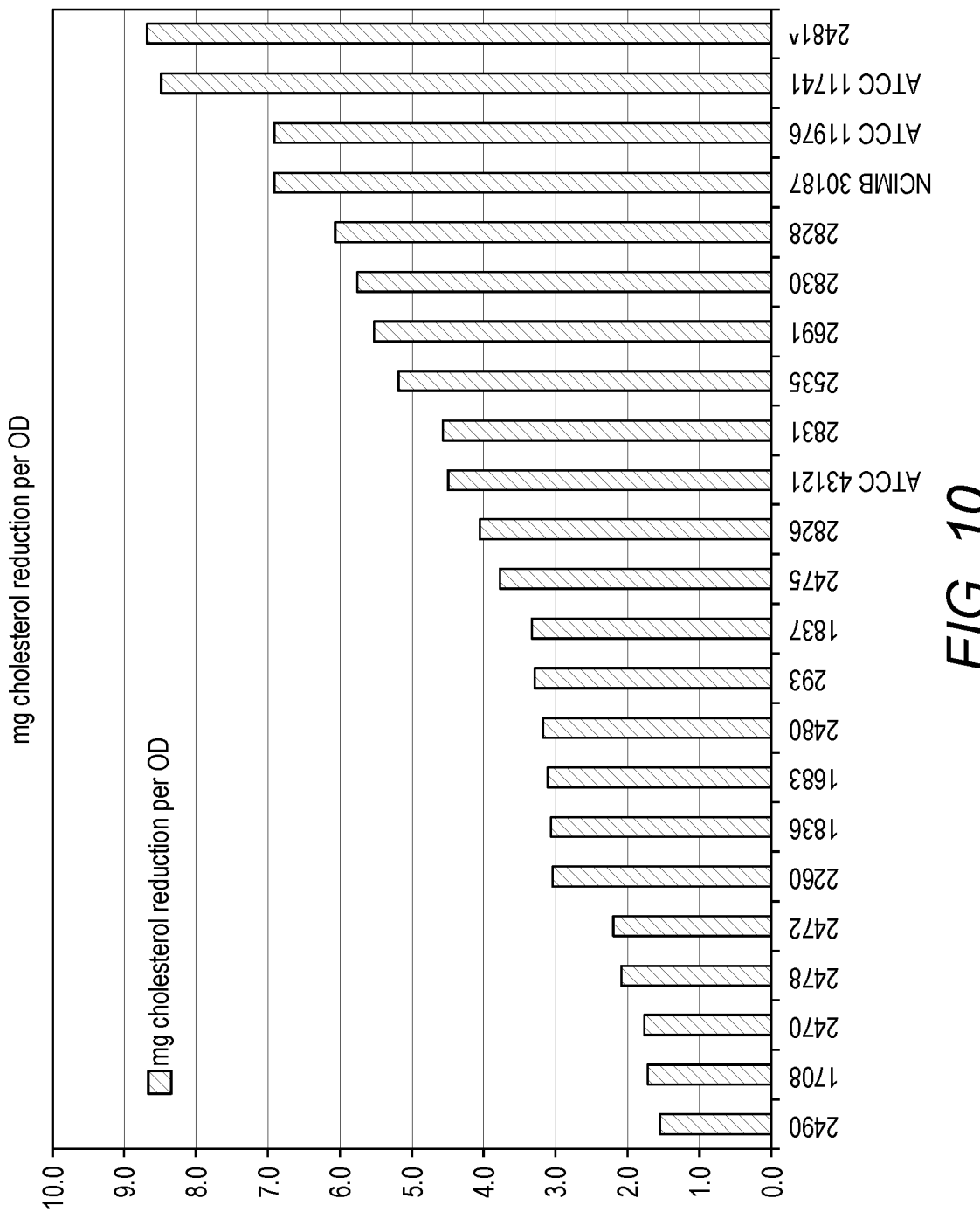
FIG. 10 is a graph of bacterial count over time using 0.1% lactose as a growth medium for *L. salivarius* in Experiment 1.

Table 4 below and FIG. 10 shows the normalized cholesterol assimilation relative to the optical density.

TABLE 4

| Strain | Biological replicate 1 OD after 24 hours growth | Biological replicate 2 OD after 24 hours growth | Biological replicate 1 Cholesterol in mg/l | Biological replicate 2 Cholesterol in mg/l | Biological replicate 1 mg reduction per OD | Biological replicate 2 mg reduction per OD | Average mg cholesterol reduction per OD |
|---|---|---|---|---|---|---|---|
| 306 | 1.58 | 1.45 | 21.0 | 19.6 | 0.8 | 1.8 | 1.3 |
| 2490 | 1.31 | 1.28 | 19.1 | 21.5 | 2.5 | 0.6 | 1.5 |
| 1708 | 2.2 | 1.9 | 18.1 | 19.4 | 1.9 | 1.5 | 1.7 |
| 2471 | 1.55 | 1.53 | 19.7 | 19.4 | 1.6 | 1.9 | 1.8 |
| 2478 | 1.56 | 1.5 | 19.0 | 19.2 | 2.1 | 2.1 | 2.1 |
| 2472 | 1.66 | 1.95 | 19.0 | 17.6 | 2.0 | 2.4 | 2.2 |
| 2260 | 3.52 | 3.62 | 11.5 | 11.3 | 3.1 | 3.0 | 3.0 |
| 1836 | 3.61 | 3.75 | 9.7 | 12.3 | 3.5 | 2.7 | 3.1 |
| 1683 | 4.28 | 3.92 | 10.6 | 8.6 | 2.7 | 3.5 | 3.1 |
| 2480 | 1.2 | 1.04 | 19.3 | 18.3 | 2.5 | 3.9 | 3.2 |
| 293 | 3.54 | 3.27 | 10.8 | 11.4 | 3.3 | 3.3 | 3.3 |
| 1837 | 3.6 | 3.72 | 10.1 | 10.0 | 3.4 | 3.3 | 3.3 |
| 2475 | 0.72 | 0.75 | 19.1 | 20.0 | 4.5 | 3.1 | 3.8 |
| 2826 | 3.28 | 4.36 | 7.3 | 6.8 | 4.6 | 3.5 | 4.0 |
| ATCC 43121 | 3.15 | 4.52 | 6.4 | 4.4 | 5.0 | 3.9 | 4.5 |
| 2831 | 3.75 | 3.81 | 4.5 | 5.5 | 4.7 | 4.4 | 4.6 |
| 2535 | 2.65 | 2.62 | 9.1 | 8.1 | 5.0 | 5.4 | 5.2 |
| 2691 | 3.12 | 2.68 | 7.1 | 5.7 | 4.9 | 6.2 | 5.5 |
| 2830 | 3.22 | 2.84 | 5.3 | 4.5 | 5.3 | 6.3 | 5.8 |
| 2828 | 3.4 | 3.02 | na* | 4.0 | | 6.1 | 6.1 |
| NCIMB 30187 | 2.75 | 2.58 | 3.5 | 4.3 | 6.8 | 7.0 | 6.9 |
| ATCC 11976 | 1.37 | 1.44 | 2.63 | 6.77 | 8.6 | 5.3 | 6.9 |
| ATCC 11741 | 1.24 | 1.33 | 3.43 | 3.50 | 8.8 | 8.2 | 8.5 |
| 2481ˆ | 1.45 | 1.42 | 1.0 | 18.4 | 14.7 | 2.7 | 8.7 |

An assessment was then made comparing the results of the strains based in % cholesterol reduction (table 5 below) and cholesterol reduction normalised to OD (table 6 below) in the context of their potential growth efficacy in the gut.

TABLE 5

(interesting candidates are underlined)

sorted by "% cholesterol reduction"

| Strain | Average % cholesterol reduction | Average mg cholesterol reduction per OD | BSH activity; week 27 (some strains did not grow - na) | | | | BSH activity - week 30 | | | | L. species |
|---|---|---|---|---|---|---|---|---|---|---|---|
| | | | TDCA | GDCA | 0.5Oxgal | 2oxgal | TDCA | GDCA | 0.5Oxgal | 2oxgal | |
| 306 | 8.9 | 1.3 | 0 | 0 | 0 | 0 | 0 | 2 | 1 | 1 | brevis |
| 2490 | 9.1 | 1.5 | 0 | 2 | 0 | 0 | 0 | 2 | 0 | 0 | plantarum |
| 2471 | 12.2 | 1.8 | 0 | 2 | 0 | 0 | 0 | 0 | 1 | 1 | plantarum |
| 2475 | 12.4 | 3.8 | 0 | 0 | 0 | 0 | 0 | 3 | 1 | 1 | plantarum |
| 2478 | 14.3 | 2.1 | 0 | 0 | 0 | 0 | 0 | 2 | 1 | 1 | plantarum |
| 2480 | 15.7 | 3.2 | 0 | 0 | 0 | 0 | 0 | 2 | 1 | 1 | plantarum |
| 1708 | 15.9 | 1.7 | 0 | 1 | 0 | 0 | 0 | 3 | 0 | 0 | brevis |
| 2472 | 17.9 | 2.2 | 0 | 2 | 0 | 0 | 0 | 2 | 0 | 0 | plantarum |
| 2260 | 48.7 | 3.0 | 0 | 3 | 1 | 0 | 0 | 3 | 0 | 0 | plantarum |
| 293 | 50.2 | 3.3 | 0 | 0 | 1 | 0 | 0 | 3 | 3 | 3 | brevis |
| 1836 | 50.5 | 3.1 | 0 | 1 | 1 | 0 | 0 | 1 | 1 | 1 | plantarum |
| 1837 | 54.7 | 3.3 | 0 | 2 | 1 | 0 | 0 | 3 | 1 | 1 | plantarum |
| 2481 | 56.3 | 8.7 | 0 | 2 | 0 | 0 | 0 | 2 | 1 | 1 | plantarum |
| 1683 | 56.9 | 3.1 | 0 | 3 | 1 | 0 | 0 | 3 | 0 | 0 | plantarum |
| 2535 | 61.4 | 5.2 | 0 | 0 | 1 | 0 | 0 | 3 | 0 | 0 | plantarum |
| ATCC 11976 | 67.3 | 6.9 | 0 | 0 | 0 | 0 | 0 | 0 | 0 | 0 | fermentum |
| 2826 | 68.2 | 4.0 | 0 | 3 | 1 | 0 | 0 | 3 | 0 | 0 | plantarum |
| <u>2691</u> | <u>71.3</u> | <u>5.5</u> | 0 | 0 | 1 | 0 | 0 | 3 | 0 | 0 | plantarum |
| <u>ATCC 43121</u> | <u>75.7</u> | <u>4.5</u> | 3 | 0 | 2 | 1 | 3 | 0 | 0 | 0 | acidophilus |
| <u>ATCC 11741</u> | 75.9 | <u>8.5</u> | na | na | na | na | 0 | 0 | 0 | 0 | salivarius |
| 2831 | 77.5 | 4.6 | na | na | na | na | 0 | 3 | 0 | 0 | plantarum |
| <u>2830</u> | <u>77.9</u> | <u>5.8</u> | 0 | 0 | 1 | 0 | 0 | 3 | 0 | 0 | plantarum |
| <u>2828</u> | <u>82.2</u> | <u>6.1</u> | 0 | 3 | 1 | 0 | 0 | 3 | 0 | 0 | plantarum |
| NCIMB 30187 | <u>82.6</u> | <u>6.9</u> | na | na | na | na | na | na | na | na | plantarum |

TABLE 6

(interesting candidates are underlined)

sorted by "mg cholesterol reduction normalized to OD"

| Strain | Average % cholesterol reduction | Average mg cholesterol reduction per OD | BSH activity; week 27 (some strains did not grow - na) | | | | BSH activity - week 30 | | | | L. species |
|---|---|---|---|---|---|---|---|---|---|---|---|
| | | | TDCA | GDCA | 0.5Oxgal | 2oxgal | TDCA | GDCA | 0.5Oxgal | 2oxgal | |
| 306 | 8.9 | 1.3 | 0 | 0 | 0 | 0 | 0 | 2 | 1 | 1 | brevis |
| 2490 | 9.1 | 1.5 | 0 | 2 | 0 | 0 | 0 | 2 | 0 | 0 | plantarum |
| 1708 | 15.9 | 1.7 | 0 | 1 | 0 | 0 | 0 | 3 | 0 | 0 | brevis |
| 2471 | 12.2 | 1.8 | 0 | 2 | 0 | 0 | 0 | 0 | 1 | 1 | plantarum |
| 2478 | 14.3 | 2.1 | 0 | 0 | 0 | 0 | 0 | 2 | 1 | 1 | plantarum |
| 2472 | 17.9 | 2.2 | 0 | 2 | 0 | 0 | 0 | 2 | 0 | 0 | plantarum |
| 2260 | 48.7 | 3.0 | 0 | 3 | 1 | 0 | 0 | 3 | 0 | 0 | plantarum |
| 1836 | 50.5 | 3.1 | 0 | 1 | 1 | 0 | 0 | 1 | 1 | 1 | plantarum |
| 1683 | 56.9 | 3.1 | 0 | 3 | 1 | 0 | 0 | 3 | 0 | 0 | plantarum |
| 2480 | 15.7 | 3.2 | 0 | 0 | 0 | 0 | 0 | 2 | 1 | 1 | plantarum |
| 293 | 50.2 | 3.3 | 0 | 0 | 1 | 0 | 0 | 3 | 3 | 3 | brevis |
| 1837 | 54.7 | 3.3 | 0 | 2 | 1 | 0 | 0 | 3 | 1 | 1 | plantarum |
| 2475 | 12.4 | 3.8 | 0 | 0 | 0 | 0 | 0 | 3 | 1 | 1 | plantarum |
| 2826 | 68.2 | 4.0 | 0 | 3 | 1 | 0 | 0 | 3 | 0 | 0 | plantarum |
| <u>ATCC 43121</u> | <u>75.7</u> | <u>4.5</u> | 3 | 0 | 2 | 1 | 3 | 0 | 0 | 0 | acidophilus |
| <u>2831</u> | <u>77.5</u> | <u>4.6</u> | na | na | na | na | 0 | 3 | 0 | 0 | plantarum |
| 2535 | 61.4 | 5.2 | 0 | 0 | 1 | 0 | 0 | 3 | 0 | 0 | plantarum |
| <u>2691</u> | <u>71.3</u> | <u>5.5</u> | 0 | 0 | 1 | 0 | 0 | 3 | 0 | 0 | plantarum |
| <u>2830</u> | <u>77.9</u> | <u>5.8</u> | 0 | 0 | 1 | 0 | 0 | 3 | 0 | 0 | plantarum |
| <u>2828</u> | <u>82.2</u> | <u>6.1</u> | 0 | 3 | 1 | 0 | 0 | 3 | 0 | 0 | plantarum |
| NCIMB 30187 | <u>82.6</u> | <u>6.9</u> | na | na | na | na | na | na | na | na | plantarum |

TABLE 6-continued (interesting candidates are underlined)

sorted by "mg cholesterol reduction normalized to OD"

| Strain | Average % cholesterol reduction | Average mg cholesterol reduction per OD | BSH activity; week 27 (some strains did not grow - na) | | | | BSH activity - week 30 | | | | L. species |
|---|---|---|---|---|---|---|---|---|---|---|---|
| | | | TDCA | GDCA | 0.5Oxgal | 2oxgal | TDCA | GDCA | 0.5Oxgal | 2oxgal | |
| ATCC 11976 | 67.3 | 6.9 | 0 | 0 | 0 | 0 | 0 | 0 | 0 | 0 | *fermentum* |
| ATCC 11741 | 75.9 | 8.5 | na | na | na | na | 0 | 0 | 0 | 0 | *salivarius* |
| 2481 | 56.3 | 8.7 | 0 | 2 | 0 | 0 | 0 | 2 | 1 | 1 | *plantarum* |

Strains 2828 (ECGC 13110403), 2830 (ECGC 13110402), 2691 (ECGC 13110401) and ATCC43121 show high cholesterol reduction and good BSH activity in both analysis above in tables 5 and 6. The in vitro tests conducted strongly suggest that these strains, whether in combination with one another or individually, would be suitable for use in modifying the absorption of cholesterol or in the treatment of heart disease, diabetes or obesity in an individual. These strains could be used in conjunction with growth specific prebiotics to encourage and support growth.

Experiments were then conducted to look at how well a number of strains coped with being freeze dried and also the subsequent BSH activity towards specific bile salts of three selected strains.

The first step was to ferment a number of strains. Strains were found to acidify all carriers and cryoprotectants chosen. It was assessed that formulations should be worked cold during production. The choice of carriers and their final concentrations were as follows: 82% MD+14% Sorbitol (MD=maltodextrin) (rest medium, and bacteria) and 82% MD+14% Sucrose. All strains grew well on the Nitrogen sources selected with a mix of Yeast extract and Soy peptone. No animal ingredients were suggested for the validation, but it was assessed that the soy peptone may cause insoluble precipitate, which could hinder the downstream processing in the future. Ideally, it was assessed that the medium to be used in production is based on 100% YE, with no other Nitrogen sources. Table 7 below shows the summary of the results of the fermentation and viability rates for the three chosen strains (B4321, B2828 and B2830) in the media. In the following data, B4321 relates to the same strain as B2691 referred to earlier.

TABLE 7

| | Strain | | | | | |
|---|---|---|---|---|---|---|
| | B4321 (B2691) | | B2828 | | B2830 | |
| | Media | | | | | |
| | Sorbitol | Sucrose | Sorbitol | Sucrose | Sorbitol | Sucrose |
| Coagulation | YES | | NO | | NO | |
| ODmax-fermentation | 9.5 | | 12.9 | | 15.7 | |
| CFU-fermentation | 7.5E+09 | | 1.4E+10 | | 1.6E+10 | |
| Cells/OD | 8E+08 | | 1E+09 | | 1E+09 | |
| Conversion factor in Carrier | 24% | 24% | 18% | 17% | 14% | 14% |
| CFU in Carrier solution (30% DM) | 3.9E+09 | 4.1E+09 | 2.1E+09 | 2.5E+09 | 1.8E+09 | 2.2E+09 |
| CFU in powder | 3.24E+09 | 4.12E+09 | 2.35E+09 | 2.82E+09 | 1.38E+09 | 2.62E+09 |
| Survival freeze drying | 28% | 34% | 39% | 39% | 27% | 41% |

Figure 11:
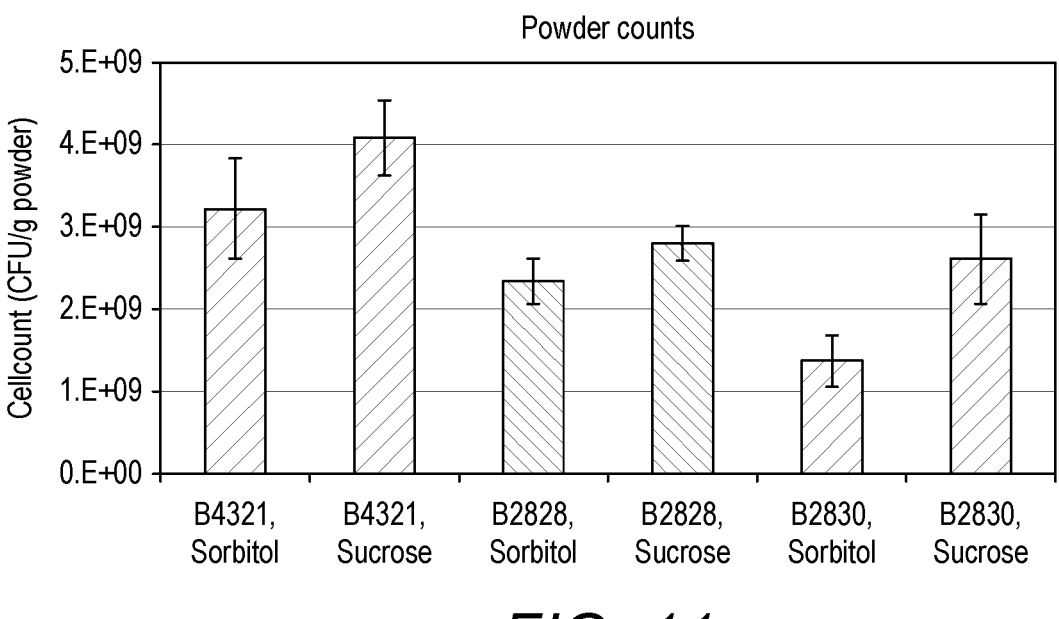
FIG. 11 is a bar chart showing the powder count of a number of strains during the freeze drying experiments.
Figure 12:
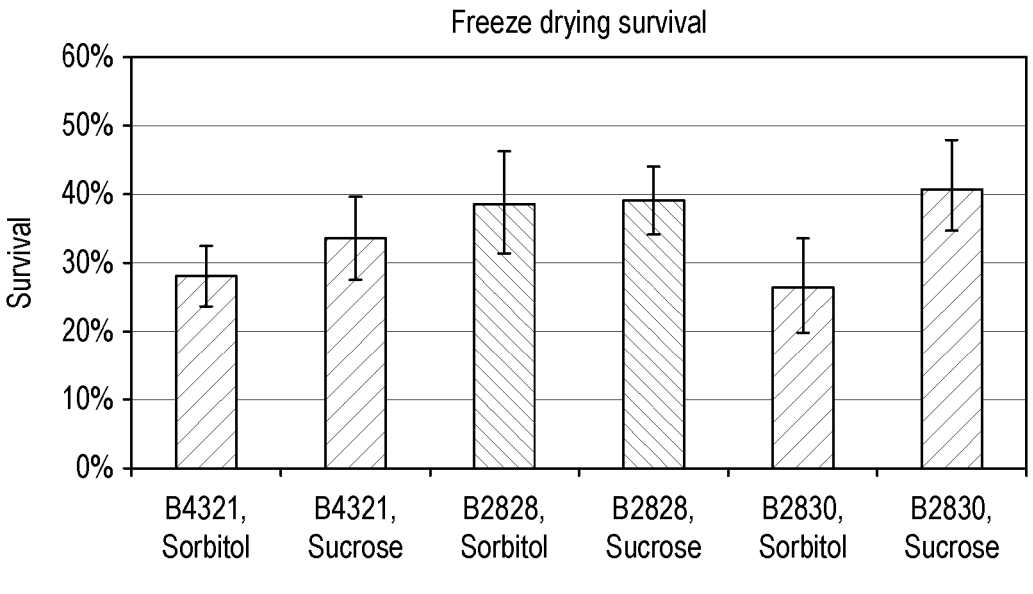
FIG. 12 is a bar chart showing the freeze drying survival of a number of strains during the freeze drying experiments.

FIG. 11 shows the powder counts for a number of strains, whereas FIG. 12 shows the freeze drying survival of those same strains.

Figure 13:
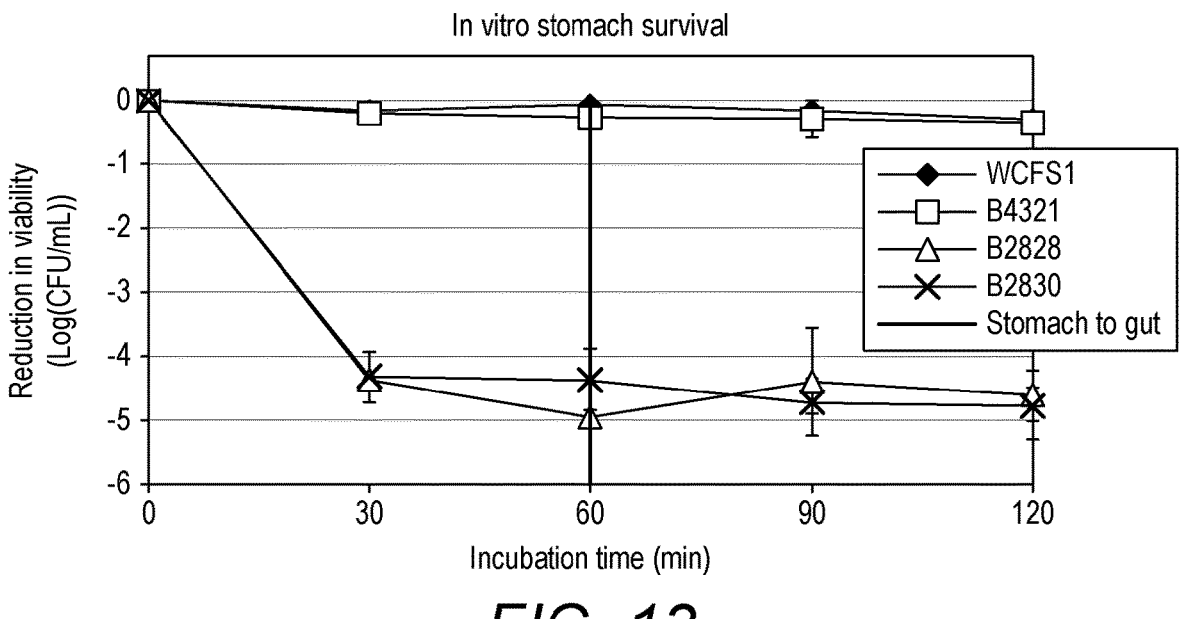
FIG. 13 is a bar chart showing the in vitro stomach survival of a number of strains which had been freeze dried.

FIG. 13 shows the survival of the strains in the stomach. Strain B4321 (B2691) clearly survives better under the conditions tested ~109 CFU/mL Stationary cells incubated for 60 min at pH 2.45 in a Na/K/HCl solution with Pepsin adn lipase.

Figure 14:
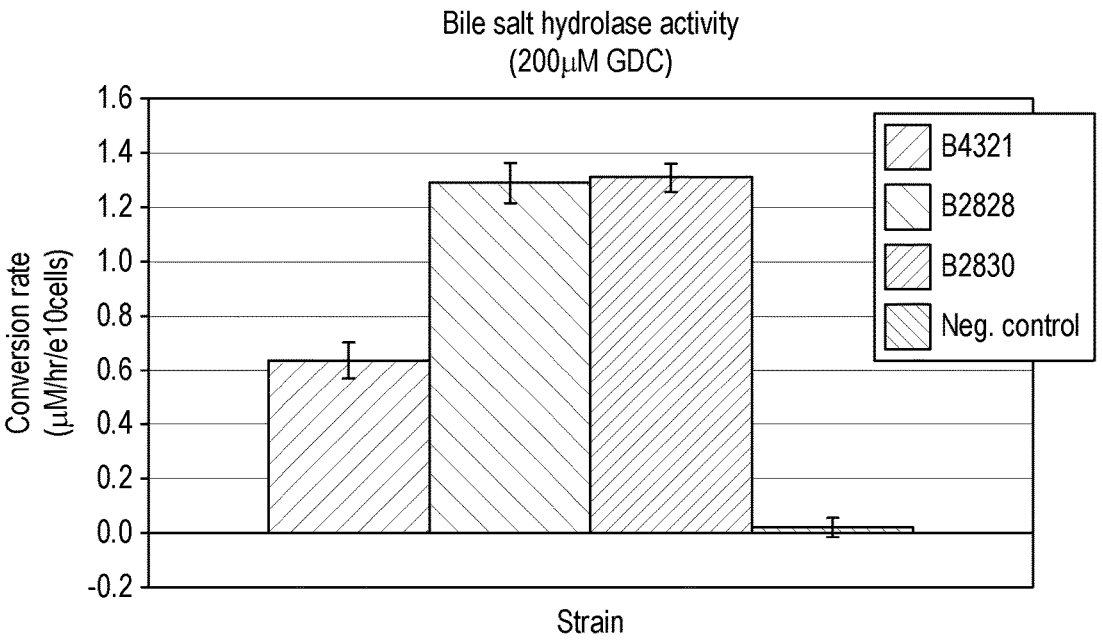
FIG. 14 is a bar chart showing the bile salt hydrolase activity at 200 μM GDC for strains B4321, B2828 and B2830.
Figure 15:
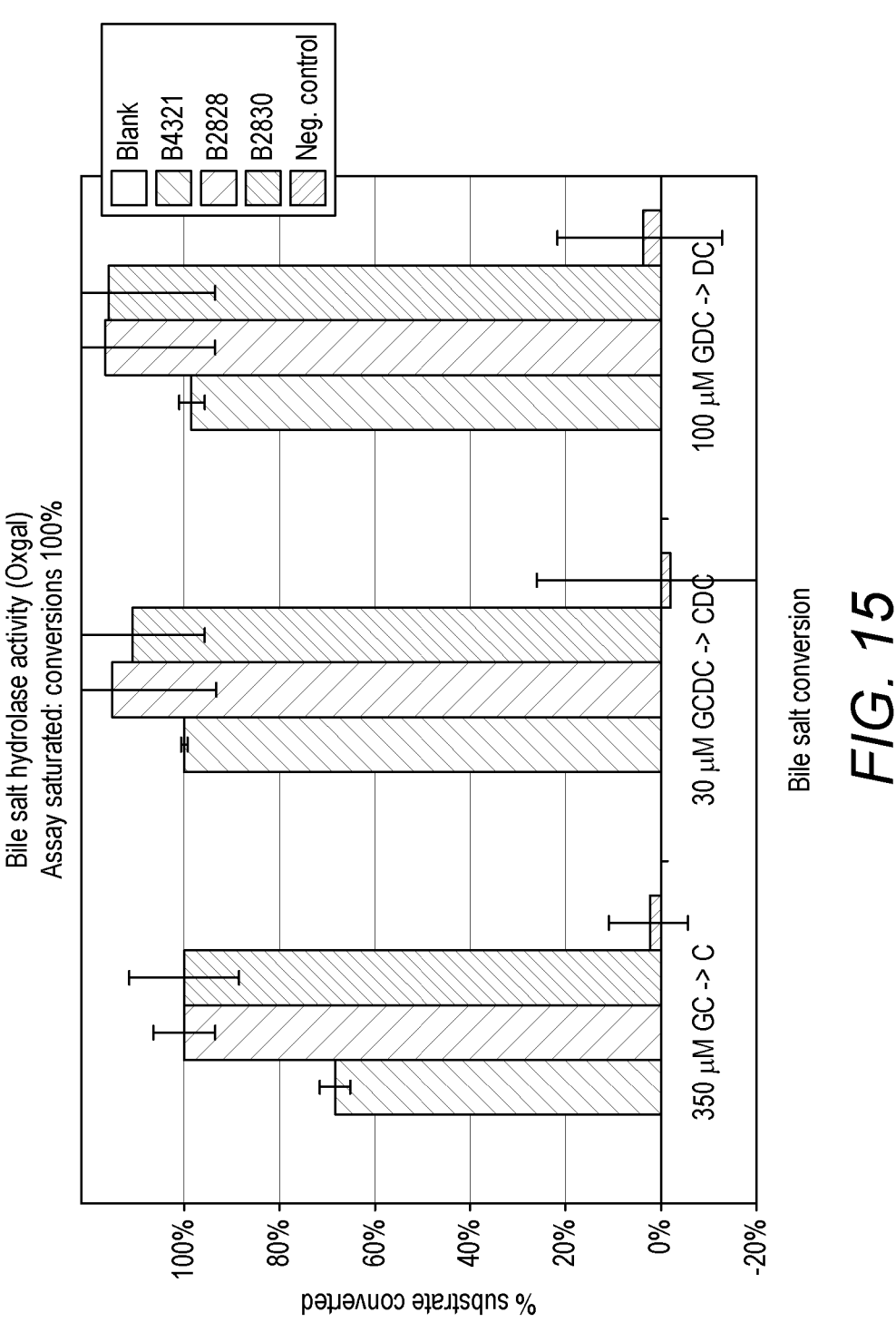
FIG. 15 is a bar chart showing the bile salt hydrolase activity (Oxgal) for strains B4321, B2828 and B2830.

FIGS. 14 and 15 show the Bile Salt Hydrolase activity on the chosen strains. B2828 and B2830 converted nearly 100% of the substrate in 3 hrs. Therefore no discrimination appeared to be possible between these strains.

The forgoing embodiments are not intended to limit the scope of the protection afforded by the claims, but rather to describe examples of how the invention may be put into practice.

Deposition of Biological Material

A deposition of biological material was made for the purposes of a United Kingdom patent application at the National Collection of Type Cultures (NCTC) in the UK. The NCTC is a recognised International Depository Authority (IDA) under the Budapest Treaty.

Each of the strains deposited at the NCTC in the UK have been assigned a number with the prefix ECGC. ECGC stands for European Culture General Collection.

It should be noted that B2691 (ECGC 13110401) was originally phenotypically classified as a *L. reteri* upon deposition at the NCTC. It has subsequently been found to be a *L. plantarum* based upon genetic analysis and this strain is referred to in this application as B2691 and renamed B4321 in later experiments.

The invention claimed is:

1. A composition comprising a strain of *Lactobacilli* having an elevated bile salt hydrolase activity and a galactooligosaccharide; wherein the strain is *Lactobacillus plantarum* 2830 (ECGC 13110402), wherein the galactooligosaccharide is produced by the strain by reverse β-galactosidase reaction, and wherein the composition further comprises an excipient and/or carrier compound;

the composition is in the form of a food stuff or a food additive;

the *Lactobacillus plantarum* 2830 is freeze-dried;

the composition further comprises at least one selected from: vitamins, minerals, phytochemicals and/or antioxidants; or a combination thereof.

2. The composition of claim 1 for modifying the absorption of cholesterol in an individual.

3. The composition of claim 1 for treatment of high cholesterol, heart disease, diabetes or obesity.

4. The composition of claim 1, wherein the galactooligosaccharide comprises a selective growth medium for the strain of *Lactobacilli*.

5. The composition of claim 1, wherein the composition is encapsulated.

6. The composition of claim 1, in the form of a foodstuff and/or for use as a dietary supplement.

7. The composition of claim 1, further comprising a prebiotic.

8. A method of producing a composition, the method comprising: mixing a composition according to claim 1 with a cholesterol modifying agent in a biologically effective amount.

\* \* \* \* \*